(12) United States Patent
Marlin et al.

(10) Patent No.: US 10,561,800 B2
(45) Date of Patent: Feb. 18, 2020

(54) SKIN SENSORS FOR DRUG DELIVERY DEVICES

(71) Applicant: UNL Holdings LLC, New York, NY (US)

(72) Inventors: Arthur Marlin, Willow Grove, PA (US); William King, Jeffersonville, PA (US); Stefanie Hurowitz, Ft. Washington, PA (US)

(73) Assignee: UNL Holdings LLC, New York, NY (US)

( * ) Notice: Subject to any disclaimer, the term of this patent is extended or adjusted under 35 U.S.C. 154(b) by 142 days.

(21) Appl. No.: 15/507,491

(22) PCT Filed: Aug. 28, 2015

(86) PCT No.: PCT/US2015/047487
§ 371 (c)(1),
(2) Date: Feb. 28, 2017

(87) PCT Pub. No.: WO2016/033496
PCT Pub. Date: Mar. 3, 2016

(65) Prior Publication Data
US 2017/0281877 A1 Oct. 5, 2017

Related U.S. Application Data

(60) Provisional application No. 62/043,070, filed on Aug. 28, 2014.

(51) Int. Cl.
*A61M 5/32* (2006.01)
*A61M 5/315* (2006.01)
*A61M 5/20* (2006.01)

(52) U.S. Cl.
CPC ............ *A61M 5/3234* (2013.01); *A61M 5/20* (2013.01); *A61M 5/31571* (2013.01);
(Continued)

(58) Field of Classification Search
CPC ............ A61M 5/31571; A61M 5/3234; A61M 2005/208; A61M 2005/2013;
(Continued)

(56) References Cited

U.S. PATENT DOCUMENTS 7,638,958 B2 * 12/2009 Philipp ................ A61B 17/151
318/139
8,088,096 B2 * 1/2012 Lauchard ................ A61M 5/20
604/131

(Continued)

FOREIGN PATENT DOCUMENTS

WO    WO 2006/108026 A2    10/2006
WO    WO 2006/122167 A2    11/2006
(Continued)

OTHER PUBLICATIONS

European Patent Office, International Search Report in International Patent Application No. PCT/US2015/047487, dated Nov. 11, 2015, 6 pp.
(Continued)

*Primary Examiner* — Jenna Zhang
(74) *Attorney, Agent, or Firm* — Hamilton, Brook, Smith & Reynolds, P.C.

(57) ABSTRACT

A skin sensing system for a drug delivery device includes a control unit and a skin sensor comprising one or more electrodes. The skin sensor may be configured to store a threshold value associated with skin sensing, receive one or more sensed signal values from the one or more electrodes, compare the one or more sensed signal values with the threshold value, and based on the comparison, transmit a resultant signal to the control unit. The resultant signal is used by the control unit to determine whether a skin surface of a user is substantially proximate to the skin sensor upon receiving the resultant signal. A drug delivery device for sensing contact with the skin includes the skin sensing
(Continued)

system. When the skin sensor senses that the drug delivery device is in contact with a patient's skin surface, drug delivery from the device may be permitted.

17 Claims, 11 Drawing Sheets

(52) U.S. Cl.
CPC ..... *A61M 5/2053* (2013.01); *A61M 2005/208* (2013.01); *A61M 2005/2013* (2013.01); *A61M 2005/31588* (2013.01); *A61M 2205/13* (2013.01); *A61M 2205/3317* (2013.01); *A61M 2205/50* (2013.01); *A61M 2205/502* (2013.01); *A61M 2205/70* (2013.01)

(58) Field of Classification Search
CPC ................ A61M 2205/13; A61M 5/20; A61M 2205/502; A61M 2205/3317; A61M 2205/70; A61M 5/2053; A61M 2005/31588; A61M 2205/50
See application file for complete search history.

(56) References Cited

U.S. PATENT DOCUMENTS

| | | | |
|---|---|---|---|
| 8,105,277 B2 * | 1/2012 | Grober | A61B 5/150961 604/117 |
| 2004/0247016 A1 | 12/2004 | Faries, Jr. et al. | |
| 2005/0038325 A1 * | 2/2005 | Moll | A61B 5/02042 600/300 |
| 2007/0085496 A1 * | 4/2007 | Philipp | A61B 17/151 318/139 |
| 2009/0216182 A1 * | 8/2009 | Lauchard | A61M 5/20 604/65 |
| 2010/0069842 A1 * | 3/2010 | Dos Santos | A61M 5/20 604/113 |
| 2011/0078834 A1 * | 3/2011 | King | G01K 1/143 850/9 |
| 2012/0130207 A1 * | 5/2012 | O'dea | A61M 37/0015 600/309 |
| 2013/0221097 A1 * | 8/2013 | Day | A61M 5/20 235/437 |
| 2015/0045729 A1 * | 2/2015 | Denzer | A61M 5/20 206/365 |
| 2015/0273151 A1 * | 10/2015 | McLoughlin | A61M 5/20 604/66 |

FOREIGN PATENT DOCUMENTS

| | | | | |
|---|---|---|---|---|
| WO | WO 2007/088444 A1 | 8/2007 | | |
| WO | WO-2007088444 A1 * | 8/2007 | ............. | A61M 5/20 |
| WO | WO 2008/105958 A2 | 9/2008 | | |
| WO | WO-2008105958 A2 * | 9/2008 | ............. | A61M 5/20 |
| WO | WO 2012/022771 A2 | 2/2012 | | |
| WO | WO 2012/145685 A1 | 10/2012 | | |
| WO | WO 2014/066256 A1 | 5/2014 | | |
| WO | WO-2014066256 A1 * | 5/2014 | ............ | A61M 5/002 |

OTHER PUBLICATIONS

European Patent Office, Written Opinion in International Patent Application No. PCT/US2015/047487, dated Nov. 11, 2015, 8 pp.

* cited by examiner

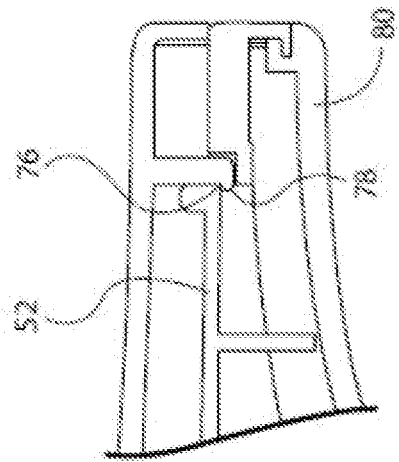
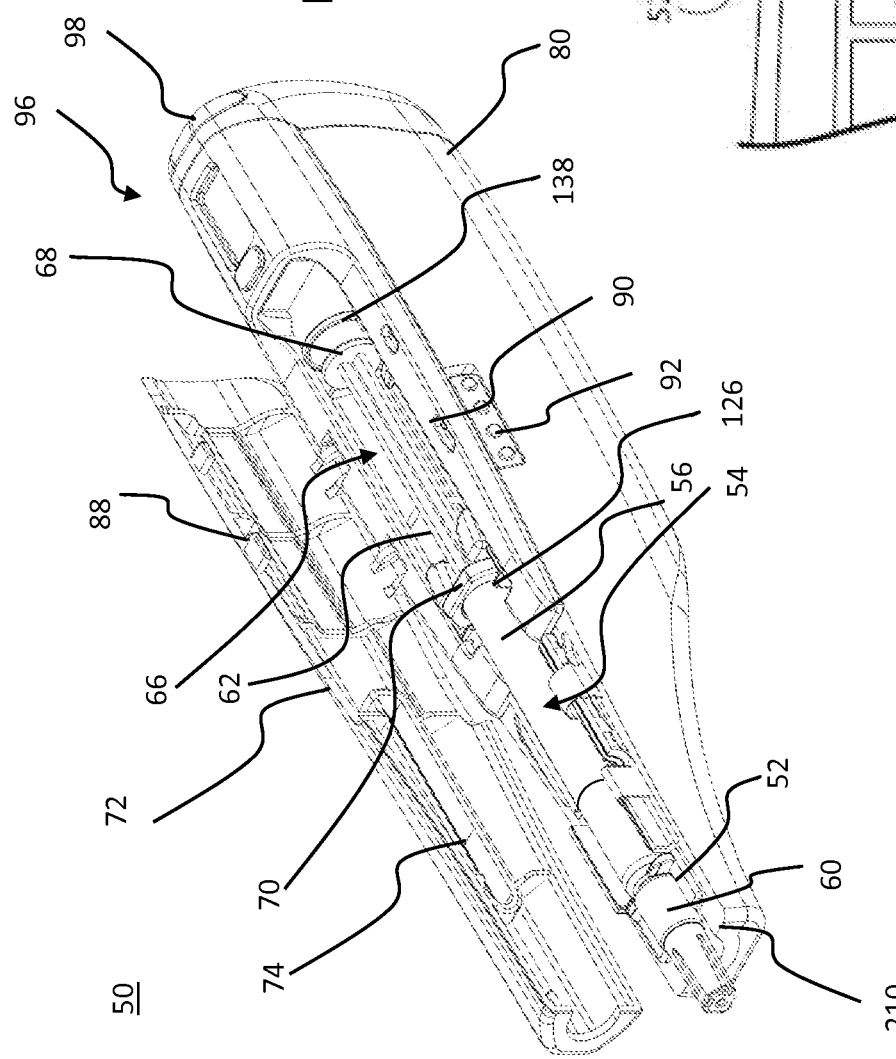

SKIN SENSORS FOR DRUG DELIVERY DEVICES

CROSS-REFERENCE TO RELATED APPLICATIONS

This patent application is a national phase application of International Patent Application No. PCT/US2015/047487, filed Aug. 28, 2015, which claims the benefit of U.S. Provisional Patent Application No. 62/043,070 filed Aug. 28, 2014, both of which are incorporated by reference herein in their entireties for all purposes.

FIELD OF THE INVENTION

The present invention relates to skin sensor systems and apparatuses. More specifically, the embodiments of the present invention are directed to electrical and electromechanical skin sensor systems for drug delivery devices. The present invention also relates to drug delivery devices, such as reusable automatic injection devices for injectable syringes, having such skin sensor systems, and their methods of use.

BACKGROUND OF THE INVENTION

Manually activated pre-filled cartridges are commercially available from a variety of manufacturers, including the owner and assignee of the present invention. Pre-filled cartridges are used in the administration of drug solutions, drug suspensions, vaccines, medicinal therapies, and any other liquid medicament by parenteral injection. Such pre-filled cartridges include a primary drug chamber, a hypodermic needle permanently affixed to and in fluid communication with the drug chamber, and a piston slidably received in the drug chamber. The pistons of the pre-filled cartridges often include a plunger sub-assembly, which may include a plunger inner and a plunger outer, to force the liquid medicament from the needle. Pre-filled cartridges are typically prepared by pharmaceutical companies or sterile filling contractors in a sterile filling room in which the drug and the cartridge are brought together in a sterile manufacturing environment wherein all components and drug solutions are isolated from microbial contamination. Currently, visual, tactile or audible indicators are generally linked to the end of stroke or some other mechanical mechanism and not to the end of dose. The integrated needle retraction syringe retracts the needle into the barrel, removing it from the patient's skin, once the dose is complete.

In contrast to manually activated pre-filled cartridges, automatic injection devices, commonly known as "auto injectors," are also available. Such auto injectors, once triggered by the user, use an automatic mechanism to insert a hypodermic needle into the recipient's flesh at the injection site and force the liquid medicament out of a medicine compartment, through the hypodermic needle, and into the recipient. In addition, some auto injectors also incorporate retraction mechanisms to automatically retract the needle after use. Auto injectors have proven particularly useful in allowing the medically untrained user to administer a parenteral injection, and can provide both psychological and physical advantages to patients.

Patients needing to inject medication for chronic disease management have used auto injectors since the first reusable auto injector was introduced in the 1990s. An auto injector provides protection for the primary container, generally a pre-filled syringe, and offers an easy way for administration of medication. These devices offer increased convenience and autonomy for patients as well as providing a competitive advantage to the pharmaceutical partner through device differentiation and increased sales by facilitating compliance of the patient to their therapy. Auto injectors may also be beneficial in delivering large volumes (up to 1 mL currently) and viscous drugs. Auto injectors also work to prevent needle stick injuries by housing the needle within a chamber, inserting the needle into the patient for drug introduction, then retracting the needle back into the housing utilizing, for example, reverse drive mechanisms.

Moreover, some auto injectors have been designed to accept commercially available, manually activated cartridges. Such configurations may be made in the form of cartridges for auto injectors (e.g., reusable auto injectors) or single-use auto injectors. The syringes developed and manufactured by the owner and assignee of the present invention offer unique and elegant integrated retraction mechanism for needle safety. A number of different syringes and cartridge configurations may be utilized in such auto injectors, including those sold by under the trade names "Unifill" and "Unifill Finesse" and covered by one or more of the following: U.S. Pat. Nos. 6,083,199, 7,500,967, 7,935,087, 8,021,333, 8,002,745, 8,052,654, 8,114,050, and 8,167,937; U.S. Patent Pub. No. 2011/0015572 and U.S. Patent Pub. No. 2013/0226084; and International PCT App. Nos. PCT/AU2010/001505, PCT/AU2010/001677, PCT/AU2011/000515, PCT/US2012/067793, and PCT/US2014/024781 all of which are incorporated herein by reference, in their entirety, for all purposes. The automatic injectors are also designed to accept a variety of syringes as filled drug-container cartridges, i.e., as pre-filled syringes, including the "Unifill" and "Unifill Finesse" syringes described herein.

Placement or orientation of the auto injector device relative to the injection site is critical for successful outcome of the drug delivery. For example, a patient may be required to place the auto injector device on the injection site so that the device remains perpendicular throughout the drug delivery process. However, stringent positional requirements of such a device may pose challenges for some patients. Particularly, due to a lapse in concentration or due to lack of dexterity, older patients may substantially tilt the auto injector device, and improperly inject the wrong tissue. This may lead to erroneous treatment, which consequently could be detrimental to the health of the patient.

To-date, auto injector devices do not provide continuous guidance associated with the positioning of the device. As a result, due to lack of assistance from the device, it may be difficult for the patient to maintain the required position or orientation of the auto injector, and the patient may improperly place the auto injector during the drug delivery period.

Therefore, there is a need for improved auto injector devices that are operable only when the devices are in contact with and/or are properly oriented with respect to the patient's skin during the drug delivery process.

BRIEF SUMMARY OF THE INVENTION

The present invention relates to automatic injection devices for drug delivery which incorporate an electronic skin sensor that may be used as an input to a drive control mechanism. The status of the electronic skin sensor may be used to enable and/or disable functions of the drive control mechanism and/or may be used to activate functions of the drive control mechanism. The status of the electronic skin sensor may also be used to activate or deactivate visual or audible status indicators. The components of the automatic injection devices are configured for repeatable functionality.

The owner and assignee of the present invention has developed syringes that offer unique and elegant integrated mechanisms for retraction of the needle and/or syringe. The automatic injectors of the present invention may be single-use devices but are, preferably, utilized as reusable automatic injectors. Accordingly, a number of single-use syringes may be employed as cartridges with the automatic injectors of the present invention. The reusable automatic injectors of the present invention could be adapted for use with any type of retractable or safety syringe, but for simplicity, the invention is described when using a syringe similar to those sold by the owner and assignee of the present invention under the trade name "Unifill." The automatic injectors are also designed to accept a variety of syringes as drug-container cartridges. Such syringes are provided herein as merely examples of syringes capable of being utilized as cartridges within auto injectors of the present invention, and the embodiments of the present invention are readily configurable to adapt or accept a broad range of syringes for drug delivery to a patient.

The inventive incorporation of an electronic skin sensor into an automatic injector may increase the safety of the user or operator by decreasing the risk of a needle-stick injury. It additionally may decrease the likelihood of expelling the contents of a syringe unintentionally or inadvertently.

In one embodiment, the present invention provides a skin sensing system for a drug delivery device that comprises a control unit and a skin sensor. The skin sensor may include one or more electrodes. The skin sensor may be configured to: store a threshold value associated with skin sensing. The skin sensor may receive one or more sensed signal values from the one or more electrodes. The skin sensor may also be configured to compare the one or more sensed signal values with the threshold value, and based on the comparison, the skin sensor transmits a resultant signal to the control unit. The resultant signal may then be used by the control unit to determine whether a skin surface of a user is substantially proximate to the skin sensor upon receiving the resultant signal.

In another embodiment, the skin sensing system may determine that the skin surface of the user is substantially proximate to the sensor when the resultant signal indicates that the one or more sensed signals received from the respective one or more electrodes are above the threshold value.

The skin sensing system may also include a display unit which may be coupled to the control unit. In some embodiments, based on the determination, the skin sensing system may cause the display unit to display a first status notification indicating that the skin surface of the user is substantially proximate to the skin sensor.

Yet in another embodiment, the skin sensing system may determine that the skin surface of the user is not substantially proximate to the sensor when the resultant signal indicates that the one or more sensed signals received from the respective one or more electrodes are below the threshold value. Based on the determination, the control unit may cause the display unit to display a second status notification indicating that the skin surface of the user is not substantially proximate to the skin sensor.

In some implementations, the skin sensing system may include a cartridge sensor. In such implementations, the control unit of the drug delivery device may be further configured to determine an operational status of a presence of the cartridge based on a cartridge status signal received from the cartridge sensor.

In another implementation, the skin sensing system may comprise a cartridge cover sensor. In that implementation, the control unit may be configured to determine another operational status of a cartridge cover based on a cartridge cover status signal received from the cartridge cover sensor, and after the determination of the operational status of the cartridge sensor.

In some embodiments, the skin sensing system may provide the user with a user prompt to activate one or more operations of the system upon determination that: (a) the cartridge is present indicated by the cartridge status signal, (b) the cartridge cover is closed indicated by the cartridge cover status signal, and (c) after the reception of the resultant signal from the skin sensor. The control unit may cause at least one or more of the operations including injection of a needle into the skin surface based on instructions received from the user in response to the user prompt.

In another embodiment, the skin sensing system may monitor the skin sensing during a drug delivery process. During the drug delivery process the control unit may determine that the skin sensor is substantially proximate to the skin surface based on the resultant signal from the skin sensor indicating that the one or more sensed signal values are within a fluctuation window of electrode signal values. The fluctuation window may include a range of electrode signal values that are stored in the skin sensor and are calculated as percentages of the threshold value. Moreover, the range of values may include an upper limit defined by a percentage of the threshold value and a lower limit defined by another percentage of the threshold value.

In some embodiments, the skin sensing system may determine that the skin sensor is not substantially proximate to the skin surface during the drug delivery when the resultant signal indicates that the one or more sensed signals is at least below the lower limit of the fluctuation window. The control unit, in some examples, based on the determination that the skin sensor is not substantially proximate to the skin surface during the drug delivery, may cause a drive unit to retract a needle from the skin surface of the user.

In one embodiment, the skin sensing system may cause the display unit to display a guidance message to re-position the skin sensing system prior to the retraction of the needle and before the one or more sensed signals falls below the lower limit of the fluctuation window. Moreover, in some embodiments, the threshold value may be selected to be stored in the skin sensor from a group consisting of: (a) predetermined skin sensing threshold values determined by an administrator, and (b) calibrated skin sensing threshold values that are iteratively determined by the user.

In some implementations, a method of using the skin sensing system may include storing a threshold value associated with skin sensing in a skin sensor, receiving, by the skin sensor, one or more sensed signals from one or more electrodes. The method may include comparing the one or more sensed signals to the stored threshold value and transmitting a resultant signal to a control unit based on the comparison. The method further comprises determining, by the control unit, whether a skin surface of a user is substantially proximate to the skin sensor upon receiving the resultant signal.

In another embodiment, the present invention provides an automatic injector (AI) device adapted to receive a cartridge including a barrel, a needle, and a plunger assembly including a plunger seal, the cartridge defining a longitudinal axis.

The AI device may include a housing, a cartridge carrier that may be adapted to receive at least a portion of the cartridge, and the cartridge carrier may be disposed for movement relative to the housing in a direction parallel to the longitudinal axis of the cartridge. The AI device may further include a plunger carrier disposed for movement relative to the cartridge carrier, and an elongated drive device coupled to the plunger carrier. The elongated drive device may be disposed to provide movement of the plunger carrier in a direction parallel to the longitudinal axis of the cartridge. The AI device may include a transmission assembly coupling to a motor to the elongated device, and the skin sensor, and the AI device may control the motor, based on the resultant signal received from the skin sensor.

In another embodiment, the AI device may control the cartridge carrier to move the cartridge from a first position where the needle is within the housing, to a second position where the needle extends distally from the housing.

BRIEF DESCRIPTION OF THE DRAWING(S)

The following non-limiting embodiments of the invention are described herein with reference to the following drawings, wherein:

FIG. 2 is an isometric view of an automatic injector of the present disclosure in which a cartridge is in place;

FIG. 3 is a detail view of a latch mechanism of an automatic injector of the present disclosure;

DETAILED DESCRIPTION OF THE INVENTION

Figure 1:
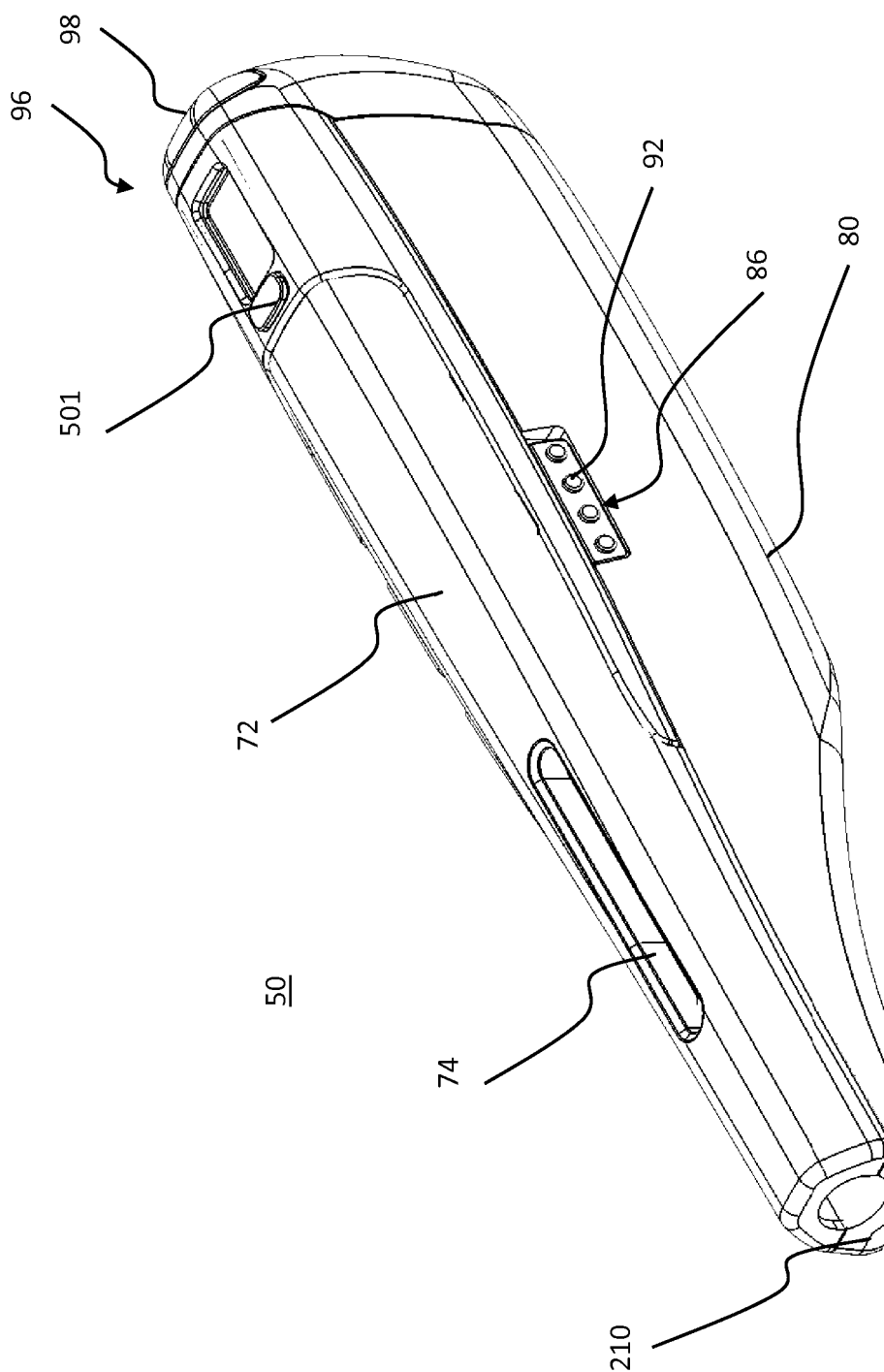
FIG. 1 is an isometric view of an automatic injector of the present disclosure.

The embodiments of the present invention relate to electronic skin sensors and their related use in automatic injection devices for drug delivery. The components of the skin sensors and automatic injection devices making use of such sensors are configured for repeatable functionality, and the automatic injectors are designed to accept a variety of drug containers, such as syringes, as cartridges. For the purposes of this disclosure, the term "cartridge" will refer generically to both syringes, which include a plunger rod for administration of a medicament from a barrel by movement of a plunger seal, and medicament containing barrels that do not include a plunger rod for activation of a plunger seal.

The automatic injectors of the present invention may be single-use devices but are, preferably, utilized as reusable automatic injectors and may additionally be wearable automatic injectors. More specifically, the embodiments of the present invention relate to electro-mechanical automatic injection devices which utilize motor-driven drive mechanisms, incorporate replaceable injection syringes, and perform one or more of the steps of: preparation and alignment of a cartridge for injection, removal of a safety cap or needle shield, detection of the presence or lack of presence of a patient's skin, continued monitoring of the presence or lack of presence of a patient's skin, needle injection, drug dose delivery, and syringe and/or needle retraction. With the incorporation of an electronic skin sensor into an automatic injector, presence of patient's skin may be detected at various operational stages of the auto injector. For example, upon the auto injector being powered on and prior to initiation of a drug delivery process, the auto injector may be in a detection mode, and may detect presence of skin, when the skin sensor is in contact with the patient's skin. A skin contact may be established when the detected electrode signal values of the skin sensor exceed a skin sensing threshold value. Once the skin contact is established, the user may initiate the drug delivery process. Upon the initiation of the drug delivery, the auto injector may configure the drive assembly (e.g., plunger and the needle) for the needle injection. The auto injector may then switch from the detection mode to a monitoring mode. During the monitoring mode, the auto injector may continuously determine whether there is any change to the established skin contact while the drug is administered to the patient by monitoring whether the detected signal values are within or outside a range of allowable electrode signal values. If the skin contact is lost (i.e., when the detected signals falls outside the range or below another skin sensing threshold value) the auto injector may notify the user, and additionally reconfigure the drive assembly so that the needle is being retracted. Optionally, the auto injector may also provide guidance related to the positioning of the auto injector with respect to the injection site or patient's skin. For example, if the auto injector detects tilting of the device based on the electrode signals received by the skin sensor, the auto injector may advise the user to reposition the device in certain directions so as to maintain the skin contact with the auto injector device during the administering of the drug. It is contemplated that, the guidance feature may be beneficial for older patients, who may not have the dexterity to maintain the required positioning of the auto injector during the drug delivery process. As such, positioning assistance provided by the auto injector may help the patient to deliver the drug successfully.

Moreover, if there is a user initiated cancelation in the middle of the drug delivery process, the auto injector may prompt the user to expend the remainder of the drug that is left in the cartridge (e.g., in a waste basket), prior to removing the cartridge from the auto injector. The drug may be expended with the cartridge in a refracted position such that the needle is not exposed to the patient. When the drug is being expended, the auto injector may further determine if the user is maintaining the skin contact with the auto injector. If the auto injector determines that a skin contact is maintained after the cancellation of the delivery process and while the remainder of the drug is being expended, the auto injector may stop the delivery process by retracting the needle or terminating drug delivery. Therefore, it will be appreciated that, during a drug delivery process, a skin contact needs to be established with the auto injector in order to commence the drug delivery process and further maintain the skin contact during the drug delivery process. However, when a drug is being expended, the skin contact with the auto injector needs to be avoided.

Therefore, by continuously monitoring the skin contact at various operation stages and providing assistance to maintain the skin contact during a drug delivery process, the incorporated skin sensors potentially reduce the potential for injuries such as needle stick injuries and thereby improve the reliability and operation of the reusable automatic injector.

As used herein to describe the electronic skin sensors, drive mechanisms, automatic injectors, cartridges, or any of the relative positions of the components of the present invention, the terms "axial" or "axially" refer generally to a longitudinal axis "A" around which the reusable automatic injector is preferably positioned although not necessarily symmetrically there-around. The terms "proximal," "rear," "rearward," "back," or "backward" refer generally to an axial direction in the direction of the plunger rod or transmission assembly. The terms "distal," "front," "frontward," "depressed," or "forward" refer generally to an axial direction in the direction of the needle or rigid needle shield. The term "laterally" refers to a direction in a plane normal to a longitudinal axis "A." The term "radial" refers generally to a direction normal to axis A.

As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration.

"Fluid" refers primarily to liquids, but can also include suspensions of solids dispersed in liquids, and gasses dissolved in or otherwise present together within liquids inside the fluid-containing portions of cartridges. The terms "drug," "medicine," and "medicament" are used to refer to any substance that is administered from a cartridge through a needle or cannula, and is not limited to pharmaceutical substances, but may include, for example, vitamins or minerals.

As used herein, the terms "automatic injector" and "auto injector" are meant to refer to the same reusable devices, which may also be referred to by the acronym "RA1".

Turning first to FIGS. 1 and 2, there is shown an automatic injector 50 according to at least one embodiment of the invention. The automatic injector 50 includes a housing 52 adapted to receive and support a syringe or cartridge 54 for injection, as well as various components of the injection system. A variety of cartridges 54 may be utilized in the reusable automatic injector 50 of the present invention, including those having automatic retraction features. For example, a safety syringe with integrated needle retraction may be used with the reusable automatic injector 50. One example of such a cartridge 54 in the form of a safety syringe is illustrated in FIG. 2, and includes a barrel 56, a needle (not shown), a rigid needle shield 60, and a plunger assembly 62 including a plunger seal 64, a plunger rod 66, and a plunger head 68. In the illustrated embodiment, the barrel 56 of the cartridge 54 includes an enlarged finger flange 70, such as is commonly used in standardized barrel 56 designs. The cartridge 54 can be pre-filled with a drug or filled at-time-of-use by a user, that is, just prior to placement within the reusable automatic injector 50. Alternate embodiments of cartridges 54 may include, by way of example only, cartridges 54 having a barrel 56 sealed by a plunger seal 64, but having no plunger rod 66, plunger head 68, or plunger assembly 62.

The housing 52 may optionally be covered by a cartridge cover 72, which may likewise be of any appropriate design. In order to allow the user to view the status of the automatic injector 50, the cartridge cover 72 may be entirely or partially translucent or transparent. Alternately, it may be entirely or partially opaque. The cartridge cover 72 of FIGS. 1 and 2 includes a window 74 that is disposed substantially adjacent the barrel 56 of a supported cartridge 54, allowing the user to view the status of drug delivery. Optionally, the window 74 or portion of the cartridge cover 72 adjacent the window may have dose indication markings to allow the user to identify the drug dose volume contained in the cartridge 54 prior to, during, and/or after drug delivery.

In the illustrated embodiment, the cartridge cover 72 is hinged to the housing 52, although an alternate arrangement may be provided. For example, either the cartridge cover 72 or the housing 52 may include mating protrusions and the other of the cartridge cover 72 or the housing 52 may include detents for receiving the protrusions. Such protrusions and detents may be provided alone, or in conjunction with a hinge arrangement, and may be provided at any appropriate location between the housing 52 and the cartridge cover 72. In one such embodiment, as shown in FIG. 3, a distal detent 76 with mating protrusion 78 may be disposed at or substantially near the distal end of the automatic injector 50 to ensure that the distal end of the cartridge cover 72 is held rigidly to the housing 52, and provide secure closure along substantially the entire contacting surface between the cartridge cover 72 and the housing 52. While the housing 52 and cartridge cover 72 may be formed as separate components, the cartridge cover 72 and the housing 52 may alternatively be formed as a single unit, coupled by a so-called living hinge (not illustrated).

The automatic injector 50 may further include a casing body 80, which provides a smooth outer appearance to the housing 52. The casing body 80 may be formed as a separate structure from the housing 52 that presents an internal chamber that receives the housing 52, or the housing 52 and the casing body 80 may be formed as a single unit. It will be appreciated that, when the automatic injector 50 includes a cartridge cover 72, the cartridge cover 72 may be coupled to the housing 52 by way of the casing body 80. That is, the cartridge cover 72 may be coupled to the casing body 80, which receives the housing 52. As with the housing 52 and the cartridge cover 72, the casing body 80 and the cartridge cover 72 may be formed separately, or as a single unit, connected, for example, by a living hinge (not illustrated).

In the embodiment illustrated in FIGS. 1-4, the cartridge cover 72 is held in a closed position over the housing 52 by a selectively actuable latch 86. In the illustrated embodiment, the cartridge cover 72 includes a protrusion 88 that is received by a recess 90 in the housing 52. A latch release 92 may be slid to the side or depressed to allow the cartridge cover 72 to be latched to or unlatched from the housing 52.

A cartridge sensor 645 (see FIGS. 2 and 6) positioned within the cartridge carrier 126 or housing 52 may optionally be utilized to sense when a cartridge 54 has been placed within the cartridge carrier 126 or housing 52 of reusable automatic injector 50. In the illustrated embodiment, the cartridge sensor is disposed at the bottom of the housing 52, although it may be alternately positioned. Placement of the cartridge 54 within the cartridge carrier 126 such that the cartridge sensor senses the presence of the cartridge 54 may provide an indication that permits the reusable automatic injector 50 to be activated.

The cartridge sensor 645 may be of any appropriate design. For example, the cartridge sensor may be a mechanical sensor, such that placement of a cartridge 54 into the cartridge carrier 126 causes the displacement of the mechanical sensor. Alternatively, or additionally, the cartridge sensor 645 may be an electrical sensor and/or an electro-mechanical sensor which may be suitably electrically coupled to a main processor system or control unit 605 of the auto injector 50, as discussed below.

Further, actuation of the cartridge sensor, whether electrical or mechanical, may be tied to operation of the automatic injector 50 such that actuation of the cartridge sensor, for example, allows the cartridge cover 72 to close and latch, or provides a signal to a processor allowing actuation of the automatic injector 50. Upon activation, the motor 106 may cause the transmission assembly 110 to drive the drive screw 114 into the correct position where the plunger interface feature of the plunger carrier 138 is in contact with, or adjacent to, the proximal end of the plunger rod 66 of the cartridge 54. Alternatively, or additionally, a cartridge cover sensor 615 (see FIG. 6) may be utilized to indicate the closing or opening of the cartridge cover 72. Cartridge cover sensor 615 may be an electrical sensor and/or an electro-mechanical sensor which may be suitably electrically coupled to a main processor or control unit 605 of the auto injector 50, as discussed below.

In order to facilitate removal of the rigid needle shield 60, the automated injector 50 may include structure that engages the rigid needle shield 60 such that movements of the cartridge 54 in the proximal direction results in removal of the rigid needle shield 60. Optionally, a needle shield sensor 625 (see FIG. 6) may be utilized to indicate the removal of the needle shield. Needle shield sensor 625 may be an electrical sensor and/or an electro-mechanical sensor which may be suitably electrically coupled to a main processor or control unit 605 of the auto injector 50.

Depending on the desired injection parameters, the drug may be immediately delivered upon injection of the needle or there may be a momentary delay between the two stages. Such parameters may be programmed into the skin sensing system or another control system of the auto injector, or separately initiated by the user, as may be desired for operation of the reusable automatic injector 50. In one example, such delay parameters and/or timing parameters may be programmed in the timer unit 630 of the skin sensing system 600.

The automatic injector 50 may further include a user interface 96 with features such as a release actuator or an activation button 501 (see FIG. 5A) that may be depressed to initiate operation of the automatic injector 50 or selection of other operative features. Other operative features may include, by way of example only, an identification of the adjustments based upon the needle utilized in the cartridge 54, or volume of medicament carried in the cartridge 54 and the volume to be dispensed, as will be explained in greater detail below. The automatic injector 50 may further include one or more lights 98, speakers (not shown), or the like, indicating the state of operation of the automatic injector 50.

Figure 4:
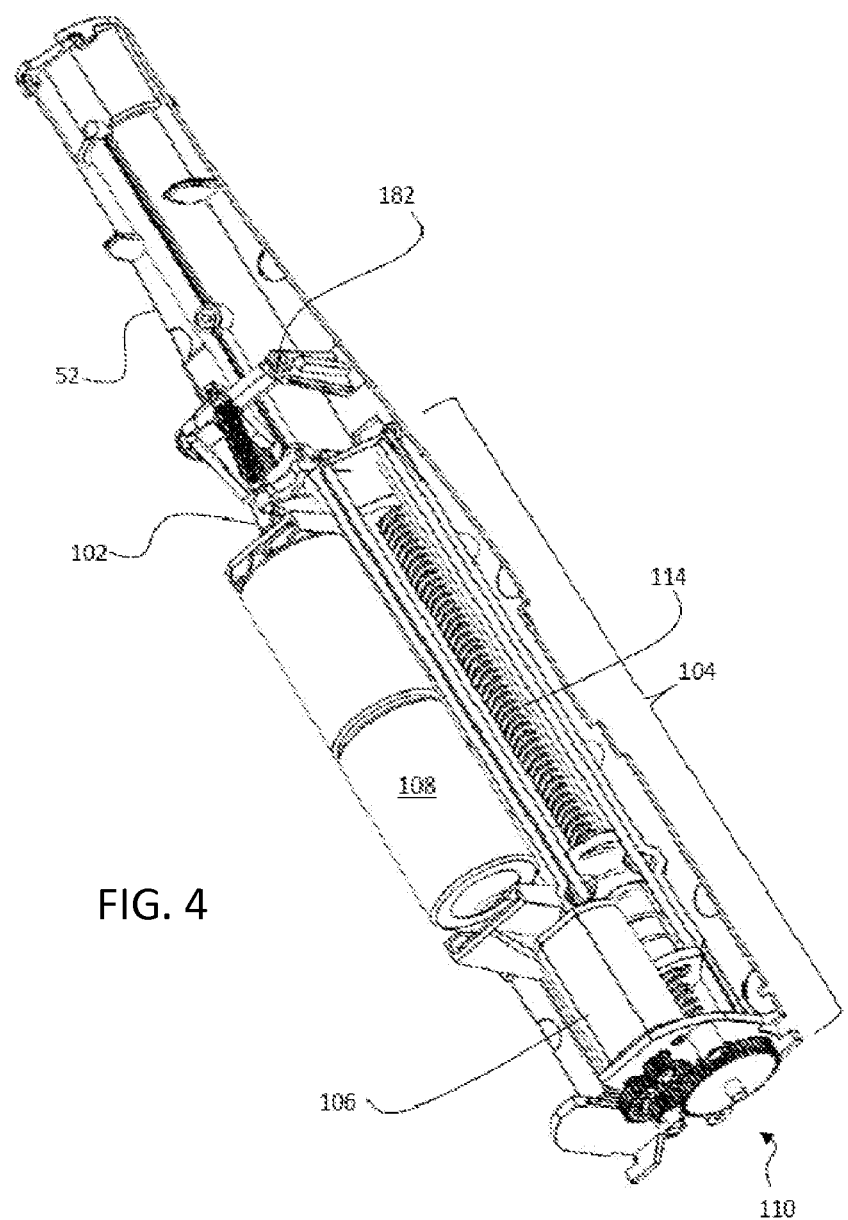
FIG. 4 is an isometric view of a subassembly of an embodiment of an automatic injector of the present disclosure.

The housing 52 may be of any appropriate design, and may be formed as a unitary structure, or it may include a plurality of components. Referring to FIG. 4, the housing 52 is an elongated frame 102 adapted to removably support a cartridge 54 along the upper surface or along structure associated with the housing 52. The housing 52 may further support one or more of the structures associated with the operation or usage of the automatic injector 50. More specifically, in the embodiment illustrated in FIG. 4, the housing 52 additionally supports a drive control mechanism 104 that controls movement of components of the cartridge 54 within the housing 52. The drive control mechanism 104 may be operated by motor 106 powered by an energy source 108. While the motor 106 and energy source 108 are illustrated as being supported on the housing 52, they could alternately be otherwise supported, for example, within a casing body 80. The energy source 108 may be in a number of different configurations and a variety of sources including, for example, disposable batteries, or rechargeable and reusable batteries. A transmission assembly 110 couples the rotary motion of the motor 106 to the drive control mechanism 104.

As discussed below, an electrical drive unit 610 (see FIG. 6) may be electrically coupled to the motor 106 and/or to the drive control mechanism 104 to control the movement of various components of the auto injector 50. Additionally, an energy source or a battery sensor 620 (see FIG. 6) may be utilized to indicate operation capability (e.g., charge remaining of the battery) of the energy source 108. The drive control mechanism 104 described and illustrated herein is for example purposes and may be of any configuration suitable for the application, for example see International PCT App. No. PCT/US2013/049314 which is incorporated herein by reference in its entirety.

Figure 5A:
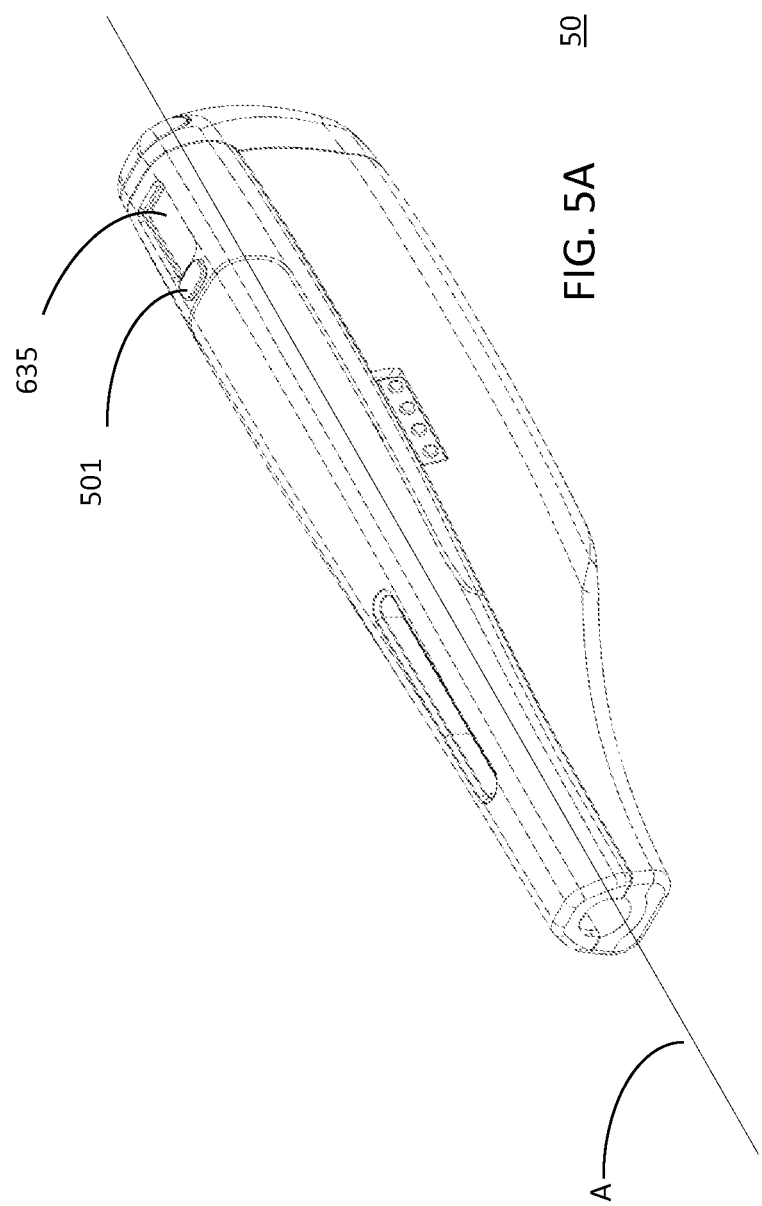
FIG. 5A is an isometric view of another embodiment of the automatic injector.

As shown in FIG. 5A, in some embodiments, auto injector 50 may include a display unit 635. The display unit may be a liquid crystal display (LCD) thin film transistor (TFT). Display unit 635 may be configured to display texts and/or graphics to provide visual information (e.g., notification) to the user. A user may also provide response to the notification by providing input to the auto injector (e.g., via activation button 501). In some implementation, the user may interact with the auto injector 50 by providing inputs via user touches and/or via a stylus using the display unit 635. In such implementations, the display unit 635 may further include capacitive or a resistive overlay. The inputs received by the display unit 635 may be processed by the auto injector control system to execute operations of the auto injector 50.

Auto injector 50 may further include activation button 501 that may be depressed to initiate operation of the automatic injector 50 or selection of other operative features. It is contemplated that, in some examples, a user may provide operational inputs to the auto injector via voice commands. In such examples, the control system may include a microphone (not shown) to process the voice commands of the user.

Figure 5B:
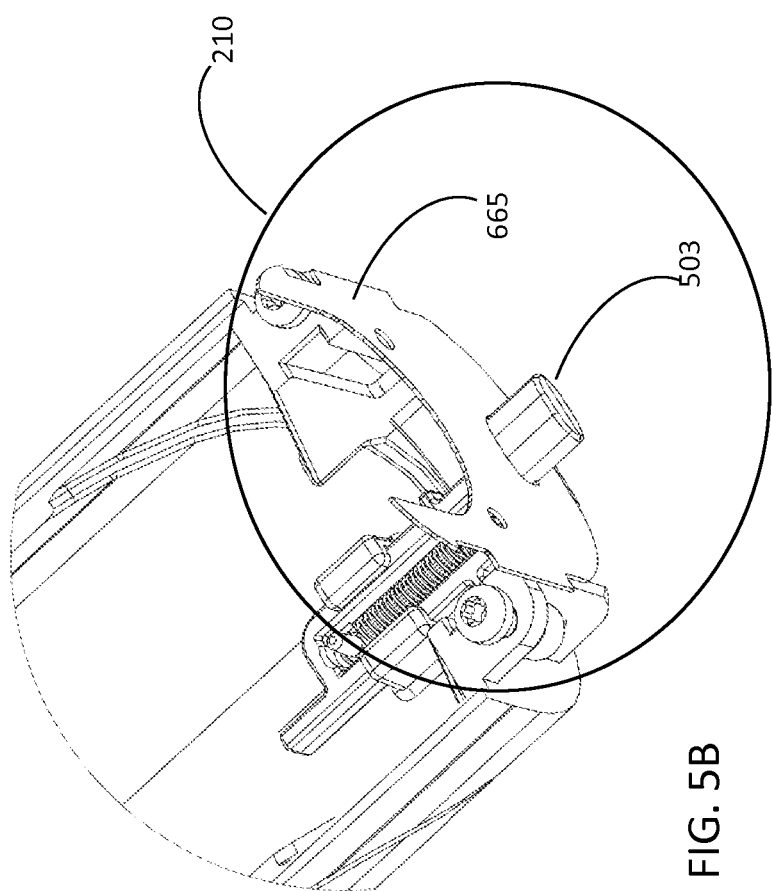
FIG. 5B is a zoom-in view of an embodiment of the automatic injector that includes an exemplary skin sensor.
Figure 5C:
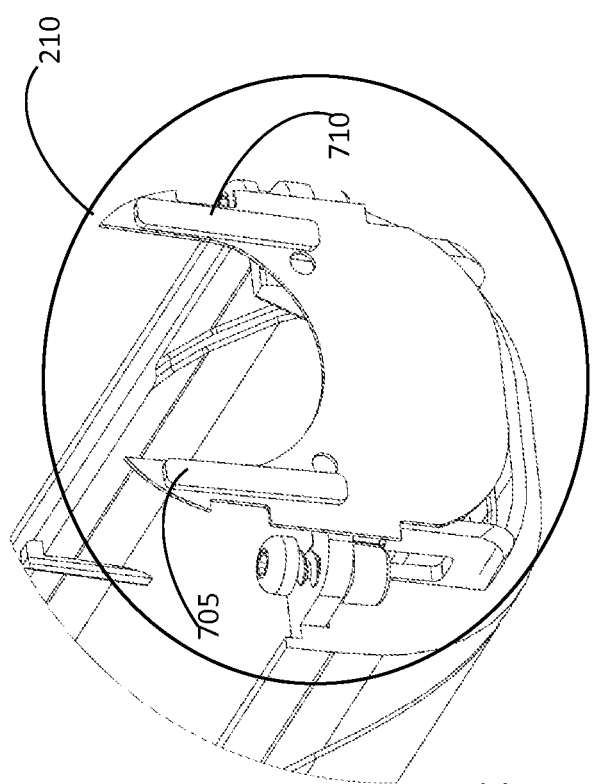
FIG. 5C is a zoom-in view of another embodiment of the automatic injector that includes an exemplary skin sensor.

FIGS. 5B-5C illustrate zoom-in views of the distal face 210 of the auto-injector 50. Auto injector 50, for example, may include one or more skin sensors 665 that may be utilized to detect or sense contact or close proximity between distal face 210 of auto injector 50 and the patient's skin prior to activation of the automatic injector (i.e., prior to a drug delivery sequence) and/or during the drug delivery sequence. One or more electrodes of the skin sensor 665 may be positioned at the distal face 210 of the reusable automatic injector 50. As shown in FIG. 5C, in one example, the auto injector may include a pair electrodes 705 and 710 positioned on the distal face 210.

As such, upon contact of distal face 210 with a portion of a patient's skin, skin sensor 665 may transmit a signal to a main control unit to indicate that the automatic injector is in position for needle insertion. The status of this signal may be used to enable and/or disable activation of the drive control mechanisms to commence insertion and/or injection upon activation by the user. The status of the signal may also be used to issue visual or audible feedback to the user to indicate to the user whether the automatic injector is in a state that allows for activation of the device. If skin contact at distal face 210 is not detected the main control unit may disable the drive mechanism (via the drive unit) so that the auto injector does not operate upon user activation. Alternatively, or additionally, the skin sensor 665 may be coupled to a mechanical interlock that prevents needle insertion and/or drug administration from the cartridge 54 unless the skin sensor 665 senses contact with the patient's skin at distal face 210. Alternatively, or in addition, skin sensor 665 may be used to detect the presence or lack of presence of skin throughout the insertion and injection processes (e.g., during the drug delivery process). If, during these processes, skin sensor 665 detects that distal face 210 has lost contact or is not substantially proximate with the patient's skin, the change in signal transmitted by skin sensor 665 to the main control unit, may cause the control system of the auto injector to stop the current operation. Additionally, or alternatively, if skin sensor 665 senses that the patient's skin is no longer in contact with distal face 210 after needle insertion has begun or has been concluded, a signal either directly from skin sensor 665 or from the main control unit, may cause the drive system to retract the needle. This provides desirable safety features which have certain benefits, including reducing the risk of needle-stick injuries. The change in status of skin sensor 665 may also cause a warning such as an audible or visual alert to be issued. For example, there may be an LED indicator light that shows green (or any alternative color) when the skin sensor senses contact with the patient's skin. This light may change colors or cease illuminating if skin contact is lost. Lights 100 may be used to indicate if the skin sensor does or does not sense skin contact.

In another implementation, a status notification may be displayed on a display unit 635 of the auto injector upon a skin contact. For example, the status notification may provide information related to the sensing of the skin portion of the patient's skin.

In some embodiments, a skin sensing system 600 is a control system that may include one or more skin sensors of the same type or a combination of different types of skin sensors. The skin sensing system may be configured for a drug delivery device, and may or may not include one or more additional control systems.

In some embodiments, the skin sensing system may include one or more skin sensors such as skin sensor 665 and a mechanical sensor 503. The mechanical sensor 503 may be a protrusion, which may depress upon being in contact with the skin of the user. The depression may in turn indicate (e.g., to the main control unit 605 or to the drive unit 610) that skin contact has been established. The mechanical sensor may be used as a redundant sensor to verify the signal transmitted by the capacitive sensor. Alternatively, the mechanical sensor may be used in the case of a malfunction of the capacitive sensor 665.

The reusable automatic injector 50 may include one or more control systems (e.g., skin sensing system 600), which may be used to control the timing and parameters of operation of the automatic injector 50. In one example, the auto injector control system may include an auto injector control unit or the main control unit that may be coupled to other control units of the various sensors. As such, operation of the control system of the auto injector may be based upon feedback from one or more sensors, such as skin sensor 665 (as shown in FIG. 5B), or input received from the user by way of the user interface 96 or activation button 501, or display unit 635. For example, the automatic injector 50 may include features that are associated with the closure of the cartridge cover 72 to the housing 52, or the position of the latch release 92. In order to minimize the opportunity for inadvertent actuation of the automatic injector 50, a cartridge cover sensor 615 may be utilized to signal whether the cartridge cover 72 is open or closed, allowing the control system to prevent actuation if the cartridge cover 72 is not closed. Similarly, the control system may prevent opening of the cartridge cover 72, that is, movement of the latch release 92, unless the internal components are in one or more particular positions.

Figure 6:
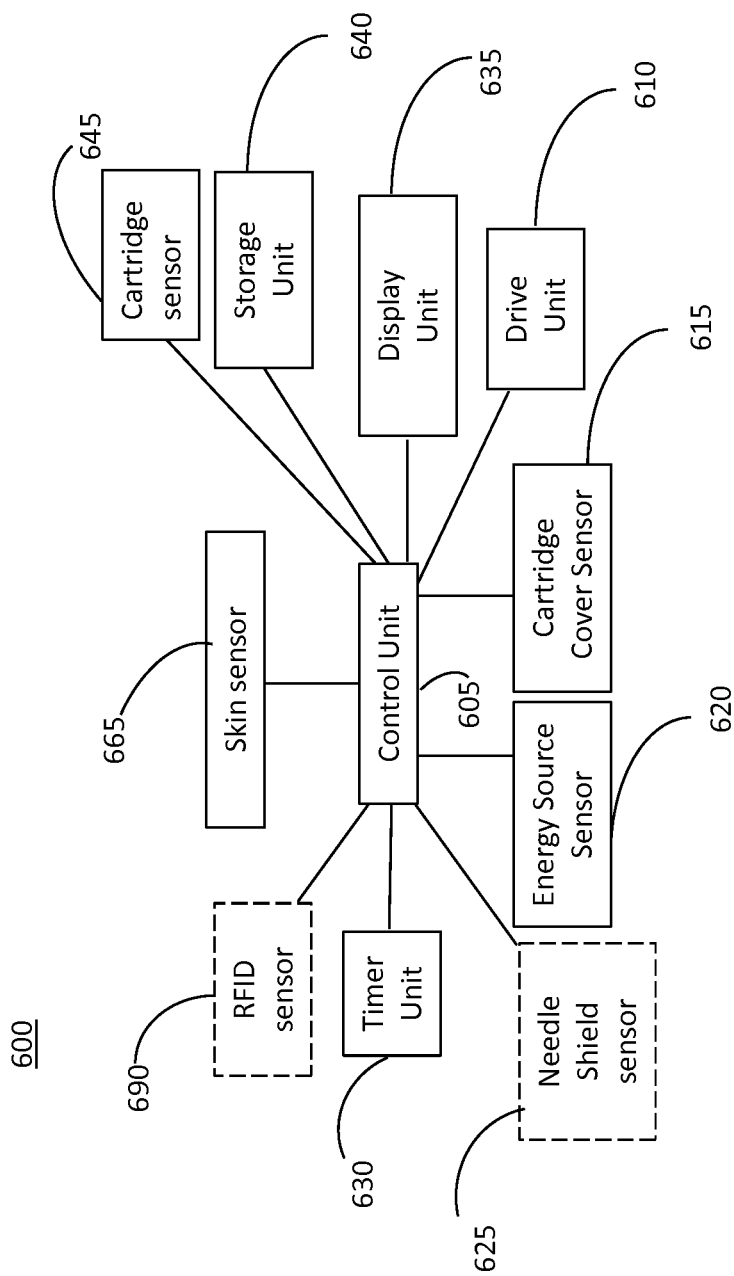
FIG. 6 is a block diagram illustrating an exemplary skin sensing system of the automatic injector.

Details are now provided of an exemplary auto injector control system of the auto injector with reference to FIG. 6.

FIG. 6 illustrates a skin sensing system 600 that may be included in the auto injector 50. The skin sensing system 600 may include one or more control units that are electronically connected to various sensors, timers and storage units of the auto injector 50.

In some implementations, skin sensing system 600 may include a main control unit 605. The main control unit 605 may include one or more controllers, microprocessors, or application specific integrated circuits (ASICs). Main control unit 605 may be implemented as hardware or a combination of hardware and software that may be programmed with instructions. The main control unit 605 may be configured to communicate, for example, by receiving and/or sending signal or data to and from the drive unit 610, cartridge cover sensor 615, energy source sensor 620, needle shield sensor 625, timer unit 630, display unit 635, storage unit 640, cartridge sensor 645, skin sensor 665 and/or RFID sensor 690. The main control unit 605 may process and interpret the data collected or monitored in order to determine and execute various functions and operations of the auto injector 50.

The main control unit 605 may be configured to receive feedback from the individual sensors, such as skin sensor 665, and to cause certain activity of the motor 106 and transmission assembly 110 based on varying feedback from one or more sensors via the drive unit 610. In at least one embodiment, the main control unit 605 is located at the proximal end of the automatic injector 50 adjacent the transmission assembly 110 and the user interface 96.

According to some embodiments of the invention, the main control unit 605 of some embodiments may be programmed to control the dose of medication administered. For example, when a cartridge 54 includes a larger volume than required for administration, the user may be directed to dispense the unneeded volume prior to placement on the target tissue. For example, the main control unit 605 via the display unit 635 may prompt the user with a notification to expend the unneeded volume. In response, the user may press the activation button 501 a predetermined number of times to dispense the unneeded volume prior to administration, for example, so long as the skin sensor 665 does not detect skin contact (i.e., as long as the main control unit 605 does not receive any signal from the skin sensor 665). Accordingly, the automatic injector 50 may be configured to expend or waste a portion of the drug dosage to the environment, prior to needle injection and drug dose delivery into a user, in order to reduce or adjust drug volume. While dispensing excess volume, the skin sensor may be in a detection or a monitoring mode to ensure that the auto injector is not held against the patient's skin. The automatic injector 50 may then be placed against the target tissue, causing the skin sensor 665 to detect the presence of the patient's skin and to issue a signal (to main control unit 605) to allow for dose administration.

It is contemplated that, in some implementations, the skin sensing system 600 may optionally include a radio frequency identity (RFID) sensor 690 which may be suitably positioned in close proximity to the cartridge carrier and may be coupled to the main control unit 605. In one example, a drug tag may be disposed or imprinted on the cartridge. The tag may be, but not limited to, a bar code, a QR code or a radio frequency identity (RFID) tag. Information related to the drug may be encrypted/encoded in the drug tag. In one example, when the cartridge is placed in the auto injector, the main control unit may cause the RFID sensor to scan the drug tag and access drug information of the drug contained in the cartridge. The drug information may include, but not limited to, drug volume, drug viscosity, drug operating temperature, expiration date, lot date, lot number, serial number, etc. of the drug or the drug cartridge.

The main control unit may decrypt or decode the drug information and process the drug information to actuate various operations related to the drug delivery. For example, based on the accessed drug information, the main control unit may determine the exact drug volume that needs to be administered and may provide instruction to the user if the drug volume needs to be adjusted prior to the administration of the drug or prior to skin sensing.

In some embodiments, drive unit 610 includes electrical circuitry and is electrically coupled to the drive control mechanism 104 which may be operated by motor 106 upon receiving instructions from the main control unit 610. Additionally, drive unit 610 may send signals to the main control unit 605 based on feedback received from the drive control mechanism 104, as discussed above.

In one embodiment, the main control unit 605 may be programmed to insert the needle, administer the programmed volume of medication, and then move the cartridge in the proximal direction to retract the needle from the target tissue by sending command signals to the drive unit 610.

According to an aspect of embodiments of the invention, the main control unit 605 of the automatic injector 50 may be configured to command or control predictable movement of a loaded cartridge 54 by sending command signal to the drive unit 610 and optionally receiving response signal from the drive unit 610. In some embodiments, the main control unit 605 may be configured to control repeatable movement, such that the automatic injector 50 may be utilized repeatedly with a plurality of cartridges 54. In those embodiments, in order to inject a patient, the automatic injector 50 may proceed through a plurality of stages that include movement of the needle into a skin surface, or target tissue or skin portion 735, and administration of an injection by movement of the plunger seal 64.

The automatic injector 50 may also include a cover release safety mechanism that prevents the cartridge cover from opening during certain stages of operation. According to at least one embodiment of the present invention, a cartridge cover release safety mechanism may be operated by the main control unit 605 by commanding the drive unit 610 as it progresses through the stages of: syringe cartridge loading, removal of rigid needle shield, needle injection, drug dose delivery, and needle and/or cartridge retraction. In other words, the main control unit 605 permits opening of the cartridge cover only when the needle is not exposed to the user, i.e., during initial loading of the cartridge when the protective needle shield is in place and/or after drug delivery and optional retraction or shielding of the needle. The main control unit 605 prevents opening of the cartridge cover during other stages of operation, i.e., when the needle is exposed for drug delivery. In this way, the cover release safety mechanism operates to inhibit the user's inadvertent exposure to the needle to reduce or eliminate accidental needle stick injuries to the user, providing a highly desirable safety feature. Particularly, to ensure cover safety mechanism, in some embodiments, the main control unit 605 communicates with cartridge cover sensor 615, as discussed below.

Cartridge cover sensor 615 may be an electrical sensor that is configured to communicate with the main control unit 605. For example, the main control unit 605 may determine whether the cartridge cover 72 is closed or open based on an operational status signal (e.g., ON/OFF) received from the cartridge cover sensor 615. Based on the determination, the main control unit 605, for example, may initiate or stop operations of the drive mechanism 104 via the drive unit 610. In one implementation, cartridge cover 72 may be a part of the drive control mechanism. As such, the cartridge cover sensor 615 may send or receive signals from the main control unit via the drive unit 610. Cartridge cover sensor 615 may or may not be included in the skin sensing system 600.

Energy source sensor 620 may be an electrical sensor that may communicate with the main control unit 605 to indicate charging capacity of the energy source 108 (e.g., how much charge is left in the battery). In one example, that main control unit 605 may receive a command signal from the user interface 96 or activation button 501 that indicates initiation of an operation of the auto injector 50, such as a drug delivery process. Upon receiving the command signal, the main control unit 605 may verify whether the energy source 108 has enough charge to complete a full drug delivery process. The main control unit 605 may consult the energy source sensor 620, or a control unit of the energy source 108 (not shown) to determine the charge capacity of the energy source 108. Alternatively, or additionally the main control unit 605 may consult the storage unit 640 that may store records of charge capacity information of the energy source 108 from previous drug delivery processes. Based on the determination, the main control unit 605 may provide notifications via the display unit 635 whether to continue the current drug delivery process or charge the energy source prior to initiation of the current drug delivery process or sequence. Battery sensor or energy source sensor 620 may or may not be included in the skin sensing system 600.

The needle shield remover may be a part of the drive control mechanism, and may include structure to engage the rigid needle shield 60 such that movements of the cartridge 54 in the proximal direction results in removal of the rigid needle shield 60. This may cause the drive unit 610 to send signals to the main control unit indicating a removal of the needle shield. Based on the determination, the main control unit 605, for example, may initiate or stop operations of the drive mechanism 104 via the drive unit 610, during or prior to a drug delivery process. Optionally, needle shield sensor 625 may be an electrical sensor that is configured to communicate with the main control unit 605. For example, the main control unit 605 may determine whether the needle shield 60 is removed or in position on the syringe needle based on an operational status signal (e.g., ON/OFF) received from the needle shield sensor 625. Needle shield sensor 625 may or may not be included in the skin sensing system 600.

Timer unit 630 may be a digital clock that may be programmed, for example, to set up time periods for various operations of the auto injector 50. For example, the timer unit 630 may be configured to indicate, to the main control unit 605, a time-out period for an operation (e.g., delay period during skin sensing, wait time after cartridge placement, etc.) or a delay period between operations (e.g., a time delay between the closing of the cartridge cover 72 and the skin sensing). In some embodiments, timer unit 630 may directly communicate with the control units of various sensors. In some implementations, the timer unit 630 may be included in the main control unit 605.

In some embodiments, display unit 635 may be LCD TFT. Display unit 635 may be electrically coupled to the main control unit 605 and may receive instructions (from the main control unit 605) to display texts and/or graphics to provide visual information (e.g., notification) to the user. A user may provide response to the notification by providing input to the auto injector (e.g., via activation button 501 and/or by interaction with display unit 635).

The display unit 635 may prompt the user to provide input for carrying out certain operations of the auto injector 50 via the display unit 635. In that example, the display unit 635 may include a graphical user interface and/or a touch screen interface that may be configured to receive input or instructions from the user. For example, the display unit 635 may provide menu options, so that the user may choose and modify various settings of the auto injector 50. Additionally, the menu options may be categorized in multiple screens, such as a home screen and a settings screen. Home screen may display options related to a current cartridge operations (e.g., verification of insertion of the cartridge in the carrier 126 and verification whether the cartridge cover is closed). Settings screen, on the other hand, may provide menu options related to language settings of the auto injector 50.

In some embodiments, the user may interact with the auto injector 50 by providing inputs via user touches and/or via a stylus. In such embodiments, the display unit may further include capacitive or a resistive overlay. The inputs received by the display unit 635 may be processed by the main control unit 605 to execute operations of the auto injector 50. Display unit 635 may or may not be included in the skin sensing system 600.

Skin sensing system 600 may include storage unit 640. Storage unit 640 may include one or more storage units, such as a random access memory (RAM) or other dynamic storage device, and/or a read only memory (ROM), and/or an electrically erasable programmable read only memory (EEPROM) for storing temporary parameters information and instructions for the main control unit 605. In some implementation, the storage unit may be implemented as a non-transitory computer readable medium which stores instructions that may be processed and executed by the control unit to control operations of the control system of the auto injector. Additionally, storage unit 640 may store error codes or error notification for various operations associated with the sensors and control unit of the auto injector 50. The error codes may be pre-programmed into the storage unit 640, for example by an administrator of the auto injector 50. In one example, main control unit 605 may retrieve the appropriate error codes, based on an error signal received from a sensor, and may further indicate an error notification to the user (e.g., via the display unit 635) related to the sensor.

In some embodiments, cartridge sensor 645 may be electrically coupled to the main control unit 605. As discussed above, placement of the cartridge 54 within the cartridge carrier 126 may cause the cartridge sensor to send a signal to the main control unit indicating the presence of the cartridge 54. Based on the received signal, the main control unit 605, for example, may activate certain operations of the auto injector 50. Cartridge sensor 645 may or may not be included in the skin sensing system 600 or another control system.

In some exemplary embodiments, auto injector 50 includes skin sensor 665. Skin sensor 665 may be, for example, a capacitive sensor, an inductive proximity sensor, an infrared sensor, an optical sensor or a thermal sensor. The skin sensor 665 may be electrically coupled to the main control unit 605. The main control unit 605 may interpret the signal generated by the skin sensor 665 and prevent and/or initiate one or more actions based on the signal received from the skin sensor 665. For example, the main control unit 605 may determine that a skin surface or skin portion of the user is in contact with the skin sensor electrodes, upon receiving a signal (e.g., a resultant signal) from the skin sensor 665. In another example, the main control unit 605 may determine that the skin portion of the user is not in contact with the electrodes, upon not receiving any signal, or upon receiving a different resultant signal from the skin sensor 665 that indicates a non-contact status with the skin of the user. Skin sensor 665 may or may not be included in the skin sensing system 600.

In one embodiment, the sensor 665 is a capacitive sensor which may be in the form of a mutual capacitance and/or a self-capacitance. The skin sensor may use charge transfer technology, surface capacitance, or projected capacitance. Skin sensor 665 may include a pair of electrodes located on the inside of the distal end face of the automatic injector 50 (see FIG. 5C). The electrodes may be affixed to the housing 52, the casing body 80, or the cartridge cover 72. The electrodes may be held in place through any means such as adhesives, glues, solders, screws, etc. The electrodes may be electrically coupled to the respective control units of the skin sensor.

It is noted that, the subject invention is described in terms of an auto injector that includes a skin sensor with a pair of electrodes that are configured for skin sensing functionalities. It is contemplated, however, that an auto injector may include a skin sensor with a single electrode, or multiple skin sensors that include respective single electrode, or a skin sensor that includes plurality of electrodes, or multiple skin sensors that include respective multiple electrodes, that may be suitably configured to achieve similar skin sensing functionalities.

Figure 7A:
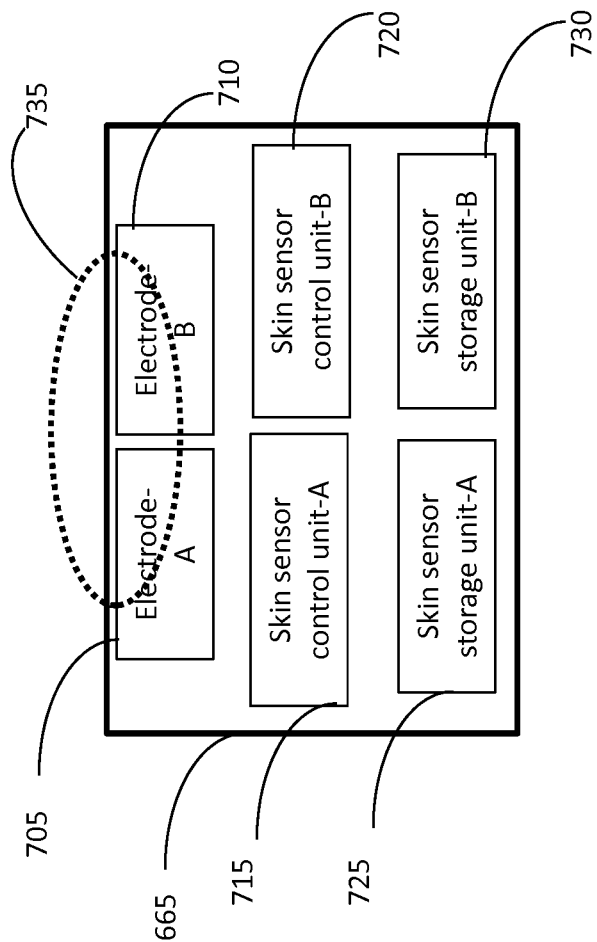
FIG. 7A is a block diagram depicting an exemplary skin sensor of the auto injector.

Details of the skin sensor 665 are now provided with reference to FIG. 7A. As mentioned above, in one exemplary embodiment, the skin sensor 665 may be a capacitive proximity sensor that includes electrode-A 705 and electrode-B 710. Skin sensor 665 further includes skin sensor control unit-A 715, skin sensor control unit-B 720, skin sensor storage unit-A 725 and skin sensor storage unit-B 730. Skin control units 715 and 720 are electrically coupled to the electrodes 705 and 710, respectively. Skin control units 715 and 720 are also electrically coupled to the skin sensor storage unit-A 725 and skin sensor storage unit-B 730, respectively.

Electrode-A 705 and electrode-B 710 may be, for example, made of copper plates or any other material that is suitable for capacitive sensing.

Skin sensor control unit-A 715 and skin sensor control unit-B 720 may be microcontrollers, microprocessors, or application specific integrated circuits (ASICs) that may be implemented as hardware or a combination of hardware and software. The control units 715 and 720 may be configured to receive signals or data from the electrodes 705 and 710, respectively, when the skin portion 735 is substantially proximate or in contact with the electrodes 705 and 710 (not shown). In some implementations, control units 715 and 720 may directly communicate with the main control unit 605.

Storage units 725 and 730 may include dynamic storage device, static storage device, and/or electrically erasable programmable read only memory device for storing temporary parameters, dynamic or static information and instructions for the skin control units 715 and 720. The control units 715 and 720 may also be configured to communicate with the storage units 725 and 735, respectively. In one example, the storage units 725 and 735 may be included in the control units 715 and 720, respectively. In some embodiments, the storage units may be configured to store a threshold value and fluctuation window values for the threshold values related to skin sensing. These values may be determined based on user studies for skin sensing, and the values may be programmed by an administrator into the auto injector (e.g., in the storage units 725 and 735) during a setup process or a manufacturing process of the auto injector 50. Discussion of threshold values are provided with reference to FIG. 7B.

Figure 7B:
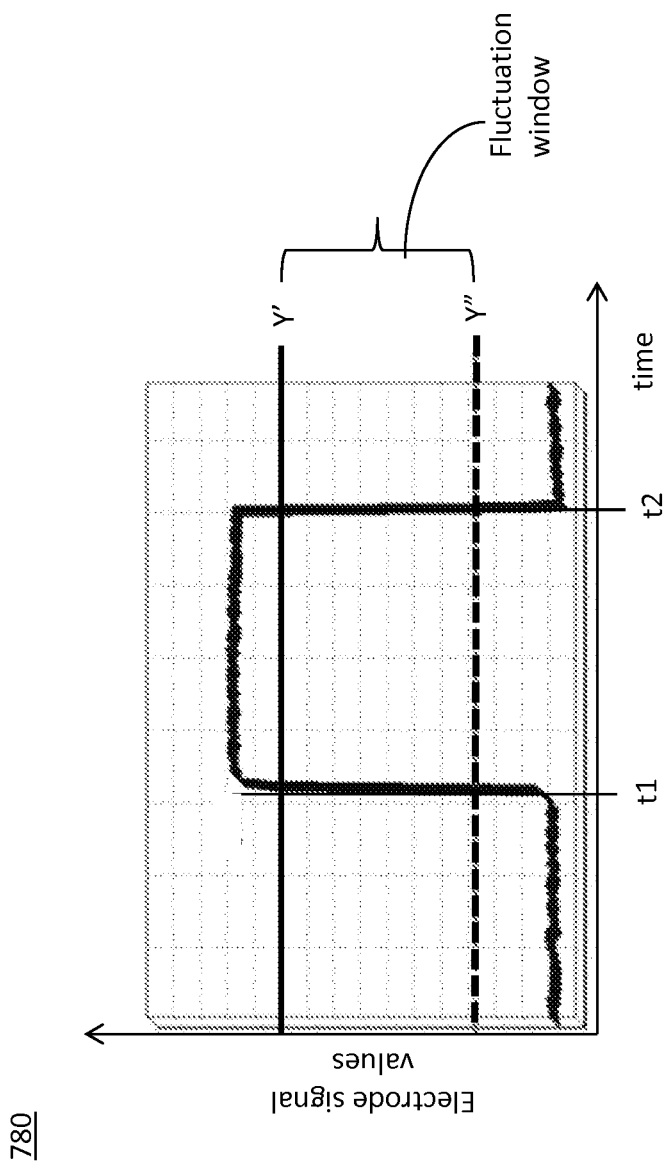
FIG. 7B is a graph showing threshold values associated with an exemplary skin sensor of the auto injector.

In FIG. 7B, graph 780 illustrates the relationship between the electrode signal values and time during a skin sensing process. Electrode signal values may be recorded when the electrodes 705 and 710 sense signals when in contact with an object (e.g., skin) over a time period. The sensed signals may be normalized and converted into digital values (i.e., the electrode signal values). In one example, the electrode signal values may be normalized capacitance values. Moreover, point Y' indicates a threshold value for skin sensing, and the fluctuation window Y'-Y" indicates a range of electrode signal values that are acceptable for skin sensing (e.g., after a skin contact has been established). In this configuration, the threshold value Y' is a discrete numerical value. The range of values may be calculated as a percentage of the threshold value Y'. As such, Y' may indicate the upper limit of the fluctuation window (e.g., an absolute threshold value) and Y" may indicate the lower limit of the fluctuation window (e.g., a percentage of the threshold value). Alternatively, the threshold value Y' may itself be measured as a first percentage of some maximum measurable value. The range of values may then be calculated as percentages of the threshold value of Y' measured as the first percentage. As such, Y' may indicate the upper percentage limit of the fluctuation window (e.g., a first percentage of some maximum measurable value) and Y" may indicate the lower percentage limit of the fluctuation window (e.g., another percentage of the maximum measurable value or a percentage of the first percentage Y').

In one example, skin sensor 665 may determine that the skin portion 735 is substantially proximate or in contact with the electrodes when the electrode signal values, received from each of the electrodes exceeds the threshold value Y' (e.g., at a time period t1-t2). The skin sensor 665 may then send a signal to the main control unit 605 to indicate that a contact has been established between the skin portion 735 and the electrodes. Once the determination has been made or the skin sensing has been established, the skin sensor 665 may continue to indicate that the electrodes are in contact with the skin portion, as long as the detected electrode signal values, from each of the electrodes 705 and 710, is within and/or above the fluctuation window Y'-Y". However, if one of the detected electrode signal values (e.g., the electrode signal value from electrode 705) falls below the point Y" while the other detected electrode signal value (e.g., the electrode signal value from electrode 710) is within the fluctuation window or above the threshold value, the skin sensor may determine that the contact with the skin portion 735 is lost (i.e., skin portion 735 is not substantially proximate to the electrodes). In some implementations, the skin sensor may determine that the contact with the skin portion is lost when both the signal values fall below Y".

It is noted that, the fluctuation window Y'-Y" accounts for permissible minor movements of the auto injector 50, while it is being held against the injection site, after the auto injector 50 has already cleared the threshold and established contact with the skin portion.

In some implementations, a user may optionally calibrate electrode signal values to set a new reference value for skin sensing. The calibration process may be performed during a setup process. In one example, the auto injector 50 may provide a setup screen on the display unit and further provide an option to calibrate the auto injector 50. Once the user chooses the option to calibrate, the auto injector may initiate a calibration mode.

The calibration may be implemented, so that the skin sensing performed by the auto injector is user-specific and accommodates user specific conditions. For example, a user may have unusual perspiring skin condition and would like to calibrate the auto injector so that it accommodates the sensing of moisturized skin. As such, during the calibration process, the user may first place the auto injector 50 against a dry skin portion and note that the auto injector 50 is sensing skin portion based on a predetermined threshold value (that was originally programmed in the storage unit of the skin sensor). Following that, the user may place the auto injector 50 against the user's moisturized skin and set or store the detected electrode signal values (detected by the electrodes) as the new baseline value for skin sensing. The user may store the new baseline value by overriding the previously stored threshold value. Alternatively, the user may store the new baseline value in addition to the previously stored threshold value. In such a case, the user may indicate that the new baseline value is the threshold value for moisturized skin and specific to the user.

Moreover, the calibration process may be repeated a few times so that an average of the detected electrode signal values may be set as the baseline/threshold value. Thus, the calibrated threshold value may take into account of the characteristics of the user's skin. Similarly, the user may further calibrate the auto injector 50 for different types of skin, so that the auto injector 50 can differentiate between the skins of an older person and a child.

It is further contemplated that, in some implementations, both of the storage units 725 and 730 may store different threshold values corresponding to various materials such as, woods, metal and clothes. The auto injector may prevent the user from calibrating the auto injector to skin sensor values near those of these materials. This may reduce the likelihood of inadvertent activation of the device.

It is contemplated that the skin sensor 665 and/or the skin sensing system 600 of the present invention may be used with wearable automatic injectors as described in PCT/US2012/53174, PCT/U52013/057259, U.S. Pat. No. 8,939,935, PCT/US2012/054861 and PCT/US2013/057327.

Figure 7C:
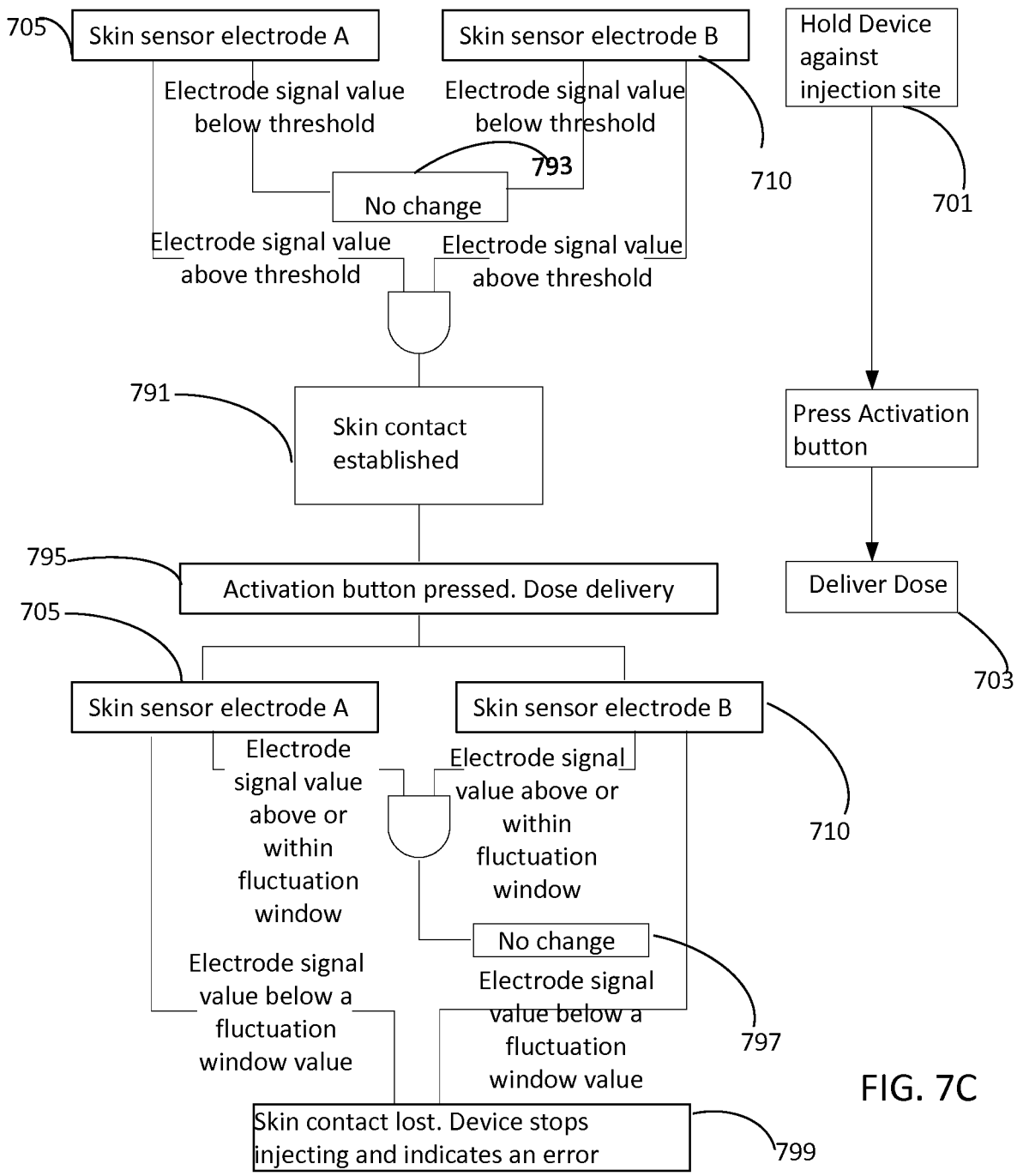
FIG. 7C is a flow chart illustrating an exemplary method for detection of skin of a user with an auto injector.
Figure 8:
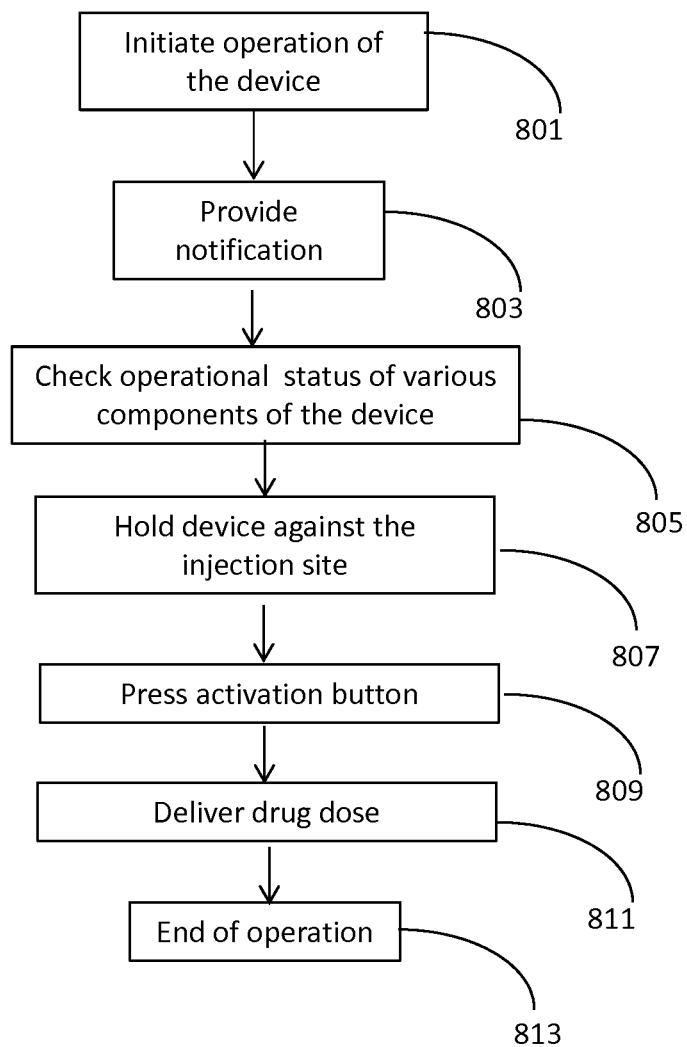
FIG. 8 is another flow chart showing an exemplary method for a drug delivery sequence.

Referring now to FIGS. 7C and 8, the process flows depicted are merely embodiments of the invention and are not intended to limit the scope of the invention. For example, the steps recited in any of the method or process descriptions may be executed in any order and are not limited to the order presented. Furthermore, it will be appreciated that the following description makes appropriate references not only to the steps depicted in FIGS. 7C-8, but also to the various system components as described above with references to FIGS. 1-7B.

Details of the operation of the skin sensor 665 are now provided with references to FIGS. 7A-7C. FIG. 7C is an exemplary flow chart/block diagram 790 that illustrates detection of skin of a user at various operational stages of the auto injector 50. For example, step 701 includes operations of the skin sensor 665, during the detection mode which is prior to an initiation of a drug dosage sequence, and while the user holds the auto injector 50 against the injection site. The detection mode is associated with the initial detection and establishment of the skin contact. Step 703 includes operations of the skin sensor 665 during the monitoring mode which is after the initiation of the drug delivery or sequence (e.g., after the user has initiated the drug delivery).

In one implementation, skin control units 715 and 720 are configured to measure or detect changes in capacitance that may arise with relation to electrodes 705 and 710, respectively when the skin portion 735 is in contact or substantially proximate to the electrodes 705 and 710 (e.g., at the distal face 210 of the auto injector). For example, electrodes 705 and 710 may be excited or charged (e.g., once the auto injector is initialized with power) and the change in the instant sensed signals or capacitance values of the electrodes 705 and 710, due to the contact with the skin portion 735 (which may or may not be grounded), may be recorded or transferred to the storage units 725 and 730 of the skin sensor 665. In one example, the recorded values may be the electrode signal values, as described above.

During the detection stage, the control units 715 and 720 may compare the instant electrode signal values (detected by the respective electrodes 705 and 710) with stored threshold value Y' (previously stored in the storage units 725 and 730) to determine whether the instant electrode signal values have exceeded the threshold values. When the detected instant electrode signal values from both the respective electrodes 705 and 710 exceed the threshold value Y' (see FIG. 7B), the skin sensor 665 determines that a skin contact has been established (box 791). In one example, the determination may be based on digital logic implemented by the skin sensor 665 (e.g., AND digital logic). Once the skin contact has been detected and established, the skin sensor 665 may send a signal to the main control unit 605, which in turn, may further instruct the display unit 635 to display a notification. For example, the notification may prompt the user to press the activation button to initiate a dosing sequence. It will be appreciated that, detection of the skin sensing may occur when the user holds the auto injector 50 perpendicularly on bare skin portion of the user (not shown).

In another example, the control units 715 and 720 may compare the instant electrode signal values (detected by the respective electrodes 705 and 710) with the stored threshold value Y' (previously stored in the storage units 725 and 730) and determine that at least one and/or both the instant electrode signal values are below the threshold value Y'. As such, the skin sensor 665 may then determine that skin portion of the user has not been detected. The skin sensor 665 may or may not send a signal to the main control to indicate there is no change in the detection or the skin has not been detected (box 793). It is noted that, a lack of detection of skin may arise due to substantial tilting of the auto injector 50. Additionally, skin sensor 665 may not detect the skin when the skin portion is partially or fully covered with objects, such as clothes.

Once the skin contact is established, and the dose sequence has been initiated (e.g., upon the activation button 501 being pressed), the auto injector device proceeds to the drug delivery phase (step 703) and switches from the detection mode to the monitoring mode. The skin sensor 665 may then continue to monitor the detection of the skin portion.

During the monitoring state, at step 703, the control units 715 and 720 may compare the instant electrode signal values (detected by the respective electrodes 705 and 710) with the fluctuation window Y'-Y" values to determine whether each of the instant electrode signal values are within the range of the fluctuation window values, and/or above the fluctuation window values. When the detected instant electrode signal values from both the respective electrodes 705 and 710 are within and/or above the fluctuation window Y'-Y" (see FIG. 7B), the skin sensor 665 determines that the skin contact, that was established earlier in the initialization or the detection stage, is being maintained (box 797). In other words, skin sensor 665 may determine that the skin portion is in contact with the electrodes when the electrode signal values are at least above the lower limit Y" (of the fluctuation window) during the delivery of the dosage. In one example, the determination may be based on an AND digital logic implemented by the skin sensor 665. The skin sensor 665 may or may not send a signal to the main control unit 605, to indicate that the skin contact is being maintained.

In another example, the control units 715 and 720 may compare the instant electrode signal values (detected by the respective electrodes 705 and 710) with the fluctuation window values and determine that at least one and/or both the instant electrode signal values are below the fluctuation window values. As such, the skin sensor 665 may then determine that skin contact is lost. In other words, skin sensor 665 may determine that the skin portion of the user is not in contact with at least one and/or both the electrodes, when one and/or both of the electrode signal values are below the lower limit Y" (of the fluctuation window) during the delivery of the dosage. The skin sensor 665 may send a signal to the main control unit 605 to indicate that the skin contact has been lost (box 799). Upon receiving the signal, the main control unit 605 may instruct the display unit 635 to display an error message indicating the loss of skin contact. Additionally, the main control unit 605 may instruct the drive unit 610 to stop any operation related to the drug dosage delivery.

It is noted that, the two electrodes (705 and 710, as shown in FIG. 5C) are disposed parallel to each other, so that the auto injector 50 would preferably be held perpendicularly against the skin portion 735 (or injection site), to ensure that only a full contact with the skin would trigger the skin sensor (e.g., when both the electrodes exceed the threshold values during the detection mode of the auto injector).

Additionally, in some implementations, during the monitoring mode, the auto injector may optionally be configured to provide guidance or assistance in relation to the positioning of the auto injector with respect the injection site. In such implementations, it is contemplated that the electrodes may be physically labelled on the distal face 210, for example, electrode-A as "1" and electrode-B as, "2". Moreover, an alert zone may be programmed in the auto injector and associated with the positioning guidance. As such, when a detected electrode signal value is within the alert zone values, an alert may be triggered. In one example, an alert zone may be programmed as 2% of the lower limit Y" of the fluctuation window.

Moreover, the auto injector may provide visual or textual notification guidance associated with the positioning or alignment of the auto injector 50 with respect to the injection site when an alert is triggered.

For example, during a monitoring stage of the skin contact, if the signal strength of one of the detected electrode signal values gets closer to the lower limit Y", that is, the detected electrode signal value lies within the alert zone, the main control unit 605 may provide an alert notification via the display unit 605 or by an audible tone. In one example, the alert notification may notify the user that the auto injector is close to losing contact with the skin.

For example, during a monitoring stage, a user may substantially tilt (e.g., by mistake) the auto injector 50 with respect to the patient's skin (e.g., towards the electrode-B, labelled "2"). As such the electrode-A 705, labelled 1, may start to lose contact with the skin portion. In other words, based on the tilting, the detected electrode signal value from the electrode 705 may fall within the alert zone.

As discussed above, scenarios where the auto injector 50 is substantially tilted may be common with older patients who may lack the dexterity to maintain the correct positioning of the auto injector during a drug delivery process. Hence, any positioning assistance provided to these patients (by the auto injector), may help these patients to successfully administer the drug.

In one example, the main control unit 605 upon determining that the electrode 705 signal value is within the alert zone, may cause the display unit to display an alert text notifying the user of the tilt. Additionally, the main control unit upon detecting the tilt (based on the signal strength values from the electrodes), may provide guidance by prompting the user to tilt back the auto injector device towards electrode-A (i.e., towards label "1"). In another example, when the electrode signal of electrode-B 710 is within the alert zone, the auto-injector may provide guidance to the user by prompting the user to tilt back the auto injector device towards electrode-B that is labelled "2". Once the signals from the electrodes are above the alert zone (i.e., the signals from the electrode 705 and 710 are not within 2% of Y"), the auto injector 50 may further notify the user that the auto injector has been appropriately re-positioned. It is noted that, the error notification and the guidance information may be suitably stored in the auto injector storage unit, and the control unit 605 may access the error notification and the guidance information appropriately.

Additionally, or alternatively, guidance may be provided via the speakers (not shown) of the auto injector. For example, in addition to the text guidance displayed in the display unit 635, a beeping tone may be used to alert or guide the user. For example, a frequency of the beeping tone may gradually increase as the auto injector 50 tilts in one direction, to alert the user. Once the auto injector 50 is re-positioned, the frequency of the beeping tone may decrease indicating that the auto injector 50 has been re-positioned.

As discussed above, during establishing a skin contact with the skin portion of the user (during the detection mode), the auto injector 50 may preferably be positioned perpendicular to the injection site. This may allow the detected electrode signal values to exceed the threshold value Y', and the control unit 605, upon determining that the skin contact has been established may cause the display unit to display a notification to the user indicating the skin contact has been established. The notification may be provided in text format. Alternatively, or additionally an audible notification may be provided via the speakers.

FIG. 8 is a flow chart of an exemplary method 800 for delivering drug to a user or to a patient with the auto injector 50. During the drug delivery process, the main control unit 605 of the auto injector 50 may verify proper operations of the various components and may provide appropriate notifications to assist the user to perform the drug delivery process. For example, the main control 605 may provide error notification, when the main control unit detects malfunction or issue with an operation of one of the components. The error notifications may be in the form of a displayed message, an audio message (e.g., beeping sounds) or a tactile notification. The main control unit 605 may then, provide further instructional messages to the user to rectify the issues of the components.

At step 801, the auto injector 50 may be initialized when a user presses the activation button 501. In one example, the main control unit 605 may power up the auto injector 50 during the initialization of the auto injector 50.

At step 803, upon receiving the activation signal, the main control unit 605 may instruct the display unit 635 to display a welcome message.

At step 805, the main control unit 605 may optionally communicate with various sensors and control units of the auto injector 50 to verify the operational status of the sensors and control units. For example, if the main control unit 605 determines that one or more sensors are not fully operational, the main control unit 605 may provide the appropriate error messages to the user via the display unit 635. The main control unit 605 may optionally control various operations of the auto injector 50 prior to, during or after the skin sensing process.

In one example, the main control unit 605 may optionally determine whether the energy source 108 has enough charge to complete a full drug delivery process. The main control unit 605 may optionally consult the energy source sensor 620, or a control unit of the energy source 108 (not shown) to determine the charge capacity of the energy source 108. Based on the determination, the main control unit 605 may provide notifications via the display unit 635. For example, if the battery has enough charge for a complete drug delivery sequence, the auto injector device may prompt the user to continue with the current drug delivery process. Alternatively, if the battery or the energy source 108 does not have enough charge, the auto injector device may display a request message to charge the battery prior to initiation of the drug delivery process.

In one example, the user may optionally proceed to load or insert the cartridge 54 on the cartridge carrier 126 and subsequently close the cartridge cover 72 (e.g., when it is determined that there is sufficient change in the energy source 108). The main control unit 605, as discussed above, may consult with the cartridge sensor 645 to ensure that the cartridge 54 is correctly in position within the cartridge carrier 126 prior to the operation.

In one implementation, the main control unit 605 may further consult with the timer unit 630 to determine whether a cartridge 54 is placed in the carrier 126 within a predetermined time. If the main control unit 605 does not receive a status signal from the cartridge sensor 645 within the predetermined time, the main control unit 605 may indicate a time-out and an appropriate error message may be displayed on the display unit 635. The user may also be prompted (on the display unit) to re-initialize the auto injector 50.

Additionally and/or alternatively, the main control unit 605 may identify that a cartridge (from a previous drug delivery sequence) is already present in the cartridge carrier, upon the initialization. As such, the user may be prompted to remove the old cartridge, in order to initiate a new drug delivery sequence with a new cartridge.

Additionally, the main control unit 605 may consult the cartridge cover sensor 615 to ensure that the cartridge cover 72 is closed prior to the drug delivery process, and/or after the cartridge is properly placed in the carrier 126. If the main control unit 605, however, determines that the cartridge cover is not closed (upon consulting with the cartridge cover sensor), the main control unit may optionally send a request to the user (via a request message in the display unit) to close the cartridge cover in order to continue with the drug delivery process.

Additionally, at step 805, the user may be prompted on the display unit 635 to remove the needle shield 60 and/or be notified that needle shield removal will commence. Once the user removes the needle shield 60, the main control unit 605, may then further prompt the user to initiate the drug delivery sequence (e.g., by pressing the activation button 501).

It is noted that, once the needle shield is removed, the cartridge needs to be used for an injection (i.e., for the drug delivery dose). If the auto injector is powered off before the dose is delivered, cartridge 54 may not be used by the auto injector 50. Accordingly, the main control unit 605 may provide the appropriate notification (e.g., via the display unit) to the user. If the needle shield has been removed, the control unit may prevent the opening of cartridge cover until the needle shield has been replaced or needle retraction has occurred.

Moreover, once the drug delivery sequence is initiated, in order to open the cartridge cover 72 and remove the cartridge 54, the user may need to cancel the injection. If the user cancels the current injection, the door open option will appear (e.g., on the display unit) and the user may then remove the cartridge from the device.

At step 807, the user may be prompted on the display unit 635 to hold the auto injector 50 against the injection site (e.g., once the cartridge 54 is properly positioned in the cartridge carrier 126 and the needle shield has been removed). For example, the main control unit 605 may instruct the display unit to display an appropriate notification for holding the auto injector 50 against the injection site. Once the user places the auto injector 50 against the injection site (e.g., the skin portion 735), the main control unit 605 determines whether the skin portion is substantially proximate or in contact with the electrodes of the skin sensor 665. Step 807 is similar to step 701 of FIG. 7C that describes skin sensing prior to a drug delivery process. Hence, for the sake of brevity, similar discussion is not provided here.

At step 809, upon determination, by the main control unit 605, that the skin portion of the user has been detected by the skin sensor 665, the main control unit 605, may prompt the user to commence the injection to the injection site. In one example, the user may respond to the prompt, by pressing the activation button 501 to initiate the drug delivery sequence.

At step 811, once the skin contact is established, and the dose sequence has been initiated, the auto injector device enters into the drug delivery phase. For example, the main control unit 605 may receive a signal from the drive unit 610 that indicates that the drug delivery process has been initiated. The main control unit 605 may then continue to monitor the detection of the skin portion (as detected at step 807), based on the communication between the main control unit 605 and the skin sensor 665. Step 811 is similar to step 703 of FIG. 7C that describes skin sensing during a drug delivery process. Hence, for the sake of brevity, similar discussion is not provided here.

It is noted that, if the user wishes to cancel the injection after the needle shield removal (and after initiating the dosing sequence), the dose must be expended or wasted before the cartridge is removed from the auto injector. Similarly, if the complete dose is not delivered, the user must waste the remaining dose before opening the cover and removing the cartridge 54 from the auto injector. For example, the main control unit 605 may receive a signal for cancellation (e.g., user may press the activation button 501 a predetermined number of times to indicate cancellation) in the middle of the drug delivery. In one example, a user may cancel a dosage upon realizing that a wrong drug is being used by mistake. In another example, the user may cancel the dosage upon realizing that he/she may not be able to complete the full dosage due to an emergency. The main control unit 605 may then prompt the user to waste the drug that is left inside the cartridge (upon receiving the cancellation signal). For example, the main control unit 605 may provide instruction such as to: remove the auto injector 50 from the injection site and go near a waste basket to expend the remaining drug that is left inside the cartridge. In this situation, the control unit may prevent disbursement of the drug if the skin sensor detects skin.

For example, upon receiving the cancellation signal of the drug delivery, and during the expending of the drug, the auto injector 50 or the main control unit 605 may be configured to monitor skin sensing (i.e., if there is any signal being transmitted from the skin sensor 665 to the main control unit 605). If the main control unit 605 receives any signal from the skin sensor during the expending of the remaining of the drug, the main control unit 605 may cause the display unit 635 to display an alert indicating that the drug is being expended on the injection site (as opposed to the waste basket). The main control unit 605 may additionally power down the auto injector if the user continues to expend the drug on the injection site.

However, if there is no cancellation of the drug delivery, at step 813, the main control unit 605 may determine that the drug has been delivered (e.g., upon receiving a signal from the drive unit 610), and may prompt the user of an end of dose notification. The main control unit 605 may optionally further prompt the user to remove the cartridge 54 after the end of dose notification. In one example, the main control unit 605 may not allow the user to shut down the auto injector 50 until the used cartridge 54 has been removed from the auto injector 50. In one example, the main control unit 605 determines an end of dose based on the distance traveled by the plunger (upon the drug delivery). Additionally, or alternatively, the distance traveled by the plunger may cause the drive unit to trigger or send a signal to the control unit 605 indicating the end of dose.

As discussed above, one or more sensors may be utilized for safety or for other reasons. For example, a skin sensor 665 may be utilized at a distal end of the reusable automatic injector 50 to ensure that it is in contact with the patient prior to needle injection. Cartridge sensor 645 may similarly be used to ensure that a cartridge 54 is correctly in position within the cartridge carrier 126 prior to operation. Other sensors known in the art may be utilized for this or other purposes and are contemplated and encompassed within the breadth of the embodiments of the present invention. Similarly, other components may optionally be utilized to enhance the safety and functionality of the automatic injector 50. For example, a cartridge ejector assembly 182 may be utilized to removably lock and eject the cartridge 54 during and after operation, respectively. One example of a cartridge ejector assembly 182 is shown in FIGS. 2 and 4. Cartridge ejector assembly 182 may be controlled by the main control unit 605 upon being coupled to the drive unit 610.

It is noted that, if a skin contact is established when the user presses the button (e.g., activation button 501) to remove the needle shield 60, the main control unit 605 may show an error notification (via the display unit 635) to prompt the user to remove the auto injector from the injection site, even though a proper skin contact has been established. Similarly, if skin contact is established when the user is in a dose wasting sequence, as discussed above, another error notification may prompt the user to remove the auto injector 50 from the injection site. Therefore, it will be appreciated that the skin sensor 665, in addition to providing determination of skin contact, may further provide safety features, based on when the skin contact is being made.

Moreover, if a safety syringe is utilized as a cartridge 54 of the automatic injector 50, safety mechanisms of the safety syringe may be triggered at the end of the drug delivery stage by operation of the syringe. In this case, drive unit 610, for example, may indicate the end of the drug delivery stage to the main control unit 605. Accordingly, the cartridge 54 disposed in the cartridge carrier 126 of the automatic injector 50 will be safe for removal and disposal by the user. Optionally, the user may reattach the rigid needle shield 60 to the distal end of the cartridge 54, such as to the distal end of the barrel 56, after the syringe has been used.

The reusable automatic injectors 50 of the present invention are able to accommodate partially or fully filled cartridges 54 of varying capacity, including 1 mL cartridges 54. The reusable automatic injector could be used with retractable or safety syringes, including prefilled syringes, as well as with non-safety syringes. When used with a non-safety syringe, the cartridge 54 is fully withdrawn back into the reusable automatic injector housing 52 after the injection or upon loss of contact of distal face 210 with the patient's skin to protect the user from exposed needles. Following the injection complete signal or upon retraction of the cartridge, the user can re-cap the non-safety syringe whilst it remains in the reusable automatic injector housing 52 with no risk of a needle-stick injury as the needle point is contained inside the housing 52. The reusable automatic injector or cartridge cover 72 can then be opened and the used cartridge 54 can be safely disposed in a sharps container. The reusable automatic injector 50 would therefore provide a safe injection for non-safety syringes in addition to working with most retractable needle syringes. The present invention also provides reusable auto injectors which are ergonomic, easy-to-use and aesthetically similar to products currently employed by self-administering patients. The automatic injectors of the present invention provide sufficient force at suitable speeds to simulate an injection by a nurse or doctor, yet provide the freedom of use for self-administering patients. The reusable automatic injectors of the present invention are also configured to withstand frequent use, such as daily use, over an extended period of time. The energy source which powers the reusable automatic injectors may similarly be replaceable, rechargeable, or otherwise provide power for use of the injectors over an extended period of time. The present invention thereby provides a reusable automatic injector with integrated safety mechanisms, enabled by incorporating a retractable needle syringe within the reusable automatic injector, in a convenient and easy-to-use package for patients.

One or more of the embodiments described above may provide additional desirable features to the patient. For example, the automatic injectors or the skin sensing system 600 of the present invention may utilize existing or additional components within the housing to limit the depth of needle insertion. In one such embodiment, features located on the housing or the guide may be utilized for this purpose. In another embodiment, mechanical limits may be integrated into the drive unit (e.g., drive control mechanism, the cartridge carrier, the plunger carrier, or the drive screw) to limit the range of travel of the syringe needle into the patient. Similarly, as described above, one or more components may be employed to automatically remove the needle shield from the syringe needle upon activation of the reusable auto injector.

In another embodiment, a single automatic injector according to the invention may be adjusted to accommodate cartridges including needles of various lengths. In this way, a single automatic injector may be utilized, for example, for intramuscular injections and subcutaneous injections. In adjusting for various needle lengths, the automatic injector may include a mechanical adjustment and/or an electrical adjustment, for example, by way of the user interface. The depth of needle insertion may be adjusted based upon the movement of the cartridge carrier within the housing.

In further embodiments, the automatic injector or the main control unit 601 may include one or more overrides. For example, the automatic injector may include an electronic override that may be actuated by way of the user interface or activation button 501. Alternatively or additionally, the automatic injector may include a manual override.

In another embodiment, the present invention relates to the method for manufacturing automatic injectors. The method includes the steps of assembling a drive control mechanism for a drive unit. The method further includes the step of attaching a guide and a support housing 52 to the drive control mechanism. The method further includes the step of installing an electronic skin sensor and the drive unit. The method may further include the steps of attaching one or more of: an energy source, a motor 106, a transmission assembly 110, and a skin sensing system such as the main control unit 605. A cartridge 54 or housing 52 cover 72 may also be attached on the top side of the automatic injector.

In yet another embodiment, the present invention relates to a method of use for an automatic injector. The method includes the steps of: inserting a cartridge 54 into the carriage contained in a housing 52 of the automatic injector, placing the automatic injector against or in close proximity to a patient's skin, and activating the automatic injector to initiate, optionally, one or more of: removal of a needle shield 60, injection of a needle into a patient, delivery of drug through the needle 58 to the patient, retraction of the needle from the patient into the housing 52, and removal of the cartridge 54 from the cartridge carrier 126. Furthermore, optionally, the method of use may include the step of expending a portion of the drug dosage to a reservoir or to the environment, prior to needle injection and drug dose delivery into a user, in order to reduce or adjust drug dose volume. Similarly, optionally, the method of use may include the step of adjusting the range of axial translation of the drive mechanism (and therefore the syringe cartridge) to accommodate different needle lengths and/or injection depths. The method may further include the steps of opening a cartridge cover 72 to access an interior of the automatic injector prior to the insertion of a cartridge 54 into the cartridge carrier 126, and the step of closing the cartridge cover 72 after the cartridge 54 has been loaded into the cartridge carrier 126. The method may similarly include the step of opening the cartridge or housing cover 72 to access an interior of the automatic injector after the refraction of the needle 58 to remove the used cartridge 54. The user may optionally reattach the needle shield 60 to the cartridge 54 prior to removal of the cartridge 54 from the cartridge carrier 126. After the used cartridge 54 has been removed from the cartridge carrier 126 of the automatic injector, the automatic injector is reset and ready to accept another cartridge 54.

The embodiments shown and detailed herein disclose only a few possible variations of the present invention; other similar variations are contemplated and incorporated within the breadth of this disclosure. As would be readily appreciated by an ordinarily skilled artisan, a number of parameters, shapes, and dimensions described above may be modified while remaining within the breadth and scope of the present invention. Such automatic injectors may be employed by, for example, patients who are required to self-inject their medication on a regular or long-term basis. Accordingly, similar to the examples provided above, the reusable auto injectors of the present invention may be configured, modified, and utilized to initiate drug delivery and activate needle retraction in any number of configurations while remaining within the breadth and scope of the present invention. Thus, it is intended that the present invention covers the modifications and variations of this invention provided they come within the scope of the appended claims and their equivalents.

The incorporation of the syringe retraction or the integrated needle retraction syringe into a reusable auto injector enables patients to safely self-administer pharmaceutical treatment in an easy-to-use manner. The incorporation of the safety syringe features and designs into the reusable automatic injector provides a true end of dose indicator. Additionally, a standard syringe may be utilized and retracted into the body of the automatic injector to provide needle safety and to indicate that the dose is complete. While the syringes described herein may have integrated safety features, the automatic injectors of the present invention may be utilized with conventional syringes that lack such features.

The incorporation of such syringes into a disposable or reusable automatic injector extends the integrated safety mechanisms of the syringes into an automated drug delivery device that is highly desirable by patients. More specifically, automatic injectors that employ the integrated needle retraction safety syringes described herein may utilize the pre-filled syringe's retraction mechanism instead of, or in addition to, other retraction mechanisms of the automatic injector such as the reverse drive mechanisms. Additionally, such automatic injectors also solve a significant unmet need for an automatic injector with a true end of dose indicator. Currently visual, tactile or audible indicators are generally linked to the end of stroke or some other mechanical mechanism and not to the end of dose. The integrated needle retraction safety syringe retracts the needle into the syringe barrel, removing it from the patient's skin, once the dose is complete. Therefore, incorporating such integrated safety syringes into an automatic injector incorporates this true end of dose indicator. The embodiments of the present invention provide electronic skin sensors, automatic injector configurations, and using reusable automatic injectors. Such devices may be employed by, for example, patients who are required to self-inject their medication on a regular or long-term basis.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A skin sensing system for a drug delivery device comprising:
   a control unit; and
   a skin sensor comprising one or more electrodes, the skin sensor configured to:
   for each of the one or more electrodes, store a threshold value associated with skin sensing;
   for each of the one or more electrodes, store a range of electrode signal values that are calculated as percentages of the respective threshold value;
   receive one or more sensed signals from the one or more electrodes;
   compare the one or more sensed signals with the respective threshold value of the one or more electrodes; and
   based on the comparison, transmit a resultant signal to the control unit, wherein the control unit is configured to:
   in a detection mode, determine whether a skin surface of a user is substantially proximate to the skin sensor based on the resultant signal indicating whether the one or more sensed signals are at or above the respective threshold value of the one or more electrodes, and in a monitoring mode, determine whether the skin sensor is substantially proximate to the skin surface based on the resultant signal indicating whether the one or more sensed signals are within a fluctuation window that includes at least a portion of the stored range of electrode values for the respective one or more electrodes.

2. The skin sensing system of claim 1, wherein the control unit determines that the skin surface of the user is substantially proximate to the skin sensor when the resultant signal indicates that the one or more sensed signals received from the one or more electrodes are above the respective threshold value of the one or more electrodes.

3. The skin sensing system of claim 2, wherein the control unit, based on the determination, causes a display unit coupled to the control unit to display a first status notification indicating that the skin surface of the user is substantially proximate to the skin sensor.

4. The skin sensing system of claim 1, wherein the control unit determines that the skin surface of the user is not substantially proximate to the sensor when the resultant signal indicates that the one or more sensed signals received from the one or more electrodes are below the respective threshold value of the one or more electrodes.

5. The skin sensing system of claim 4, wherein the control unit, based on the determination, causes a display unit coupled to the control unit to display a second status notification indicating that the skin surface of the user is not substantially proximate to the skin sensor.

6. The skin sensing system of claim 1, wherein the control unit is further configured to determine an operational status of a presence of a cartridge based on a cartridge status signal received from a cartridge sensor that is coupled to the control unit.

7. The skin sensing system of claim 1, wherein the control unit is further configured to determine another operational status of a cartridge cover based on a cartridge cover status signal received from a cartridge cover sensor that is coupled to the control unit, and after the determination of the operational status of the cartridge sensor.

8. The skin sensing system of claim 7, wherein the control unit is further configured to provide the user with a user prompt to activate one or more operations of the system upon determination that: (a) the cartridge is present indicated by the cartridge status signal, (b) the cartridge cover is closed indicated by the cartridge cover status signal, and (c) after the reception of the resultant signal from the skin sensor.

9. The skin sensing system of claim 1, wherein the control unit is further configured to cause the injection of a needle into the skin surface based on instructions received from the user in response to the user prompt.

10. The skin sensing system of claim 1, wherein the range of electrode signal values for each of the one or more electrodes includes an upper limit defined by a percentage of the respective threshold value of the one or more electrodes and a lower limit defined by another percentage of the respective threshold value of the one or more electrodes.

11. The skin sensing system of claim 10, wherein the control unit determines that the skin sensor is not substantially proximate to the skin surface during the drug delivery process when the resultant signal indicates that the one or more sensed signals is at least below the lower limit of the fluctuation window for the respective one or more electrodes.

12. The skin sensing system of claim 11, wherein the control unit, based on the determination that the skin sensor is not substantially proximate to the skin surface during the drug delivery, causes a drive unit coupled to the control unit to retract a needle from the skin surface of the user.

13. The skin sensing system of claim 12, wherein the control unit causes a display unit to display a guidance message to re-position the skin sensing system prior to the retraction of the needle and before the one or more sensed signals falls below the lower limit of the fluctuation window for the respective one or more electrodes.

14. The skin sensing system of claim 1, wherein the threshold value for each of the one or more electrodes selected to be stored in the skin sensor is from a group consisting of: (a) predetermined skin sensing threshold values of the respective one or more electrodes determined by an administrator, and (b) calibrated skin sensing threshold values of the respective one or more electrodes that are iteratively determined by the user.

15. An automatic injector (AI) device adapted to receive a cartridge including a barrel, a needle, and a plunger assembly including a plunger seal, the cartridge defining a longitudinal axis, the AI device comprising:
a housing;
a cartridge carrier adapted to receive at least a portion of the cartridge, the cartridge carrier being disposed for movement relative to the housing in a direction parallel to the longitudinal axis of the cartridge;
a plunger carrier disposed for movement relative to the cartridge carrier;
an elongated drive device coupled to the plunger carrier, the elongated drive device being disposed to provide movement of the plunger carrier in a direction parallel to the longitudinal axis of the cartridge;
a motor;
a transmission assembly coupling the motor to the elongated device; and
the skin sensing system of claim 1; wherein the control unit controls the motor, based on the resultant signal received from the skin sensor.

16. The AI device of claim 15, wherein the control unit controls the cartridge carrier to move the cartridge from a first position where the needle is within the housing, to a second position where the needle extends distally from the housing.

17. A method of sensing skin for drug delivery comprising:
for each of one or more electrodes of a skin sensor, storing a threshold value associated with skin sensing;
for each of the one or more electrodes, storing a range of electrode signal values that are calculated as percentages of the respective threshold value;
receiving, by the skin sensor, one or more sensed signals from the one or more electrodes;
comparing the one or more sensed signals to the respective threshold value of the one or more electrodes;
transmitting a resultant signal to a control unit based on the comparison; and
determining, by the control unit:
in a detection mode, whether a skin surface of a user is substantially proximate to the skin sensor based upon the resultant signal indicating whether the one or more sensed signals are at or above the respective threshold value of the one or more electrodes, and in a monitoring mode, whether the skin sensor is substantially proximate to the skin surface based upon the resultant signal indicating whether the one or more sensed signals are within a fluctuation window that includes at least a portion of the stored range of electrode signal values for the respective one or more electrodes.

\* \* \* \* \*